US006825007B2

(12) United States Patent
Zimrin et al.

(10) Patent No.: US 6,825,007 B2
(45) Date of Patent: Nov. 30, 2004

(54) THERAPEUTIC AND DIAGNOSTIC METHODS AND COMPOSITIONS BASED ON JAGGED/NOTCH PROTEINS AND NUCLEIC ACIDS

(75) Inventors: Ann B. Zimrin, Marriottsville, MD (US); Thomas Maciag, Freeport, ME (US); Michael S. Pepper, Geneva (CH); Roberto Montesano, Geneva (CH); Michael Wong, Derwood, MD (US)

(73) Assignee: Maine Medical Center Research Institute, Scarborough, ME (US)

( * ) Notice: Subject to any disclaimer, the term of this patent is extended or adjusted under 35 U.S.C. 154(b) by 0 days.

(21) Appl. No.: 10/213,329

(22) Filed: Aug. 6, 2002

(65) Prior Publication Data

US 2003/0083465 A1 May 1, 2003

Related U.S. Application Data

(62) Division of application No. 09/199,865, filed on Nov. 25, 1998, now Pat. No. 6,433,138, which is a continuation of application No. PCT/US97/09407, filed on May 30, 1997.
(60) Provisional application No. 60/018,841, filed on May 31, 1996.

(51) Int. Cl.[7] .................. C12P 21/06; C12N 15/87; C12N 1/20; C12N 15/74; C07H 21/04
(52) U.S. Cl. .................. 435/69.1; 435/455; 435/252.3; 435/320.1
(58) Field of Search .................. 536/23.5; 435/69.1, 435/252.3, 320.1, 455

(56) References Cited

U.S. PATENT DOCUMENTS

| 4,663,278 A | 5/1987 | DiNello |
| 6,004,924 A | 12/1999 | Ish-Horowicz et al. |
| 6,433,138 B1 * | 8/2002 | Zimrin et al. |

FOREIGN PATENT DOCUMENTS

| EP | 125023 | 11/1984 |
| EP | 173494 | 5/1986 |
| EP | 184187 | 6/1986 |
| WO | WO86/01533 | 3/1986 |

OTHER PUBLICATIONS

Branch AD. A good antisense molecule is hard to find. Trends Biochem Sci. 23(2):45–50, 1998.*
Mountain A. Gene therapy: the first decade. Trends Biotechnol. 18(3):119–128, 2000.*
Artavanis–Tsakonas and Simpson, 1991, Trends Genet. 7:403–408.
Artavanis–Tsakonas et al., 1995, Science 268:225–232.
Baker et al., 1990, Science 250:1370–1377.
Benoist and Chambon, 1981, Nature, London 290:304–310.
Better et al., 1988, Science 240:1041–1043.
Bierkamp and Campos–Ortega, 1993, Mech. Dev. 43:87–100.
Blank et al., 1992, TIBS 17:135–140.
Bollon et al., 1980, J. Clin. Hematol. Oncol. 10:39–48.
Bork, 1993, Proteins 17:363–374.
Botstein et al., 1982, Miami Wntr. Symp. 19:265–274.
Carson and Haudenschild, 1986, In Vitro 22:344–354.
Cenatiempo, 1986, Biochimie 68:505–516.
Chan et al., 1979, Microvasc. Res. 18:353–369.
Chobanian et al., 1986, Hypertension 8:15–21.
Coffman et al., 1990, Science 249:1438–1440.
del Amo et al., 1992, Development 115:737–744.
Ding et al., 1992, J. Biol. Chem. 267:2804–2812.
Ellisen et al., 1991, Cell 66:649–661.
Engval et al., 1972, Immunol. 109:129–135.
Folkman and Haudenschild, 1980, Nature 288:551–556.
Folkman et al., 1983, Science 221;719–725.
Folkman and Klagsbrun, 1987, Science 235:442–447.
Fourough et al., 1993, J. Biol. Chem. 268:2960–2968.
Fortini and Artavanis–Tsakonas, 1993, Cell 75:1245–1247.
Friesel et al., 1995, FASEB J 9:919–925.
Friesel et al., 1987, J. Cell Biol. 104:689–696.
Garfinkel et al., 1994, Proc. Natl. Acad. Sci. USA 91:1559–1563.
Garfinkel et al., 1992, J. Biol. Chem. 267:24375–24378.
Gilman et al., 1984, Gene sequence 32:11–20.
Glick and Whitney, 1987, J. Ind. Microbiol. 1:277–282.
Gold, et al., 1981, Ann. Rev. Microbiol. 35:365–403.
Gottesman, 1984, Ann. Rev. Genet. 18:415–442.
Greenwald 1994, Curr. Opinion In Gen. and Dev. 4:556–562.
Greenwald and Rubin, 1992, Cell 68:271–281.
Gurnkowski et al., 1987, Blood Vessels 24:11.
Gurdon, 1992, Cell 68:185–199.
Harner and Walling, 1982, J. Mol. Appl. Gen. 1:273–288.
Haudenschild et al., 1981, Hypertension 3:148–153.
Henderson et al., 1994, Development 120:2913–2924.
Hla and Maciag, 1990, Biochem. Biophys. Res. Commun. 167:637–643.
Hla et al., 1995, Biochim. Biophys. Acta 1260:227–229.
Hla and Maciag, 1990, J. Biol. Chem. 265:9308–9313.
Hla and Neilson, 1992, Proc. Natl. Acad. Sci. USA 89:7384–7388.
Hodgson, 1991, Biotechnology 9:609–613.

(List continued on next page.)

Primary Examiner—Christina Chan
Assistant Examiner—Maher Haddad
(74) Attorney, Agent, or Firm—Morgan, Lewis & Bockius, LLP

(57) ABSTRACT

This invention relates to therapeutic and diagnostic methods and compositions based on Jagged/Notch proteins and nucleic acids, and on the role of their signaling pathway in endothelial cell migration and/or differentiation. In addition, this invention provides a substantially purified Jagged protein, as well as a substantially purified nucleic acid molecule or segment thereof encoding Jagged protein, or a functionally equivalent derivative, or allelic or species variant thereof.

14 Claims, 18 Drawing Sheets

OTHER PUBLICATIONS

Hodgson, 1990, Biotechnology 8:1245–1247.
Imamura et al., 1990, Science 249:1567–1570.
Ingber and Folkman, 1989, J. Cell Biol. 109:317–330.
Izaki, 1978, Jpn. J. Bacteriol. 33:729–742.
Jarriault et al., 1995, Nature 377:355–358.
Jasny, 1987, Science 238:1653.
Jaye et al., 1985, Science 228:882–885.
Jennings et al., 1994, Development 120:3537–3548.
John et al., 1986, Rev. Infect. Dis. 8:693–704.
Johnston et al., 1982, Proc. Natl. Acad. Sci. 79:6971–6975.
Kasprzak et al., 1989, Biochemistry 28:9230–9238.
Kendall et al., 1987, J. Bacteriol. 169:4177–4183.
Kopan et al., 1996, Proc. Natl. Acad. Sci. USA 93:1683–1688.
Kopan et al., 1994, Development 120:2385–2396.
Kopczynski et al., 1988, Genes Dev. 2:1723–1735.
Lardelli and Lendahl, 1994, Exp. Cell Res. 204:364–372.
Lardelli et al., 1994, Mech. Dev. 46:123–136.
Lindsell et al., 1995 Cell 80:909–917.
Liu et al., 1987, Proc. Natl. Acad. Sci. USA 84:3438–3443
Liu et al., 1987, J. Immunol. 139:3521–3526.
Lutz et al., 1988, Exp. Cell Res. 175:109–124.
Maciag et al., 1981, J. Cell Biol. 91:420–426.
Maciag et al., 1982, J. Cell Biol. 94:511–520.
Maciag, 1984, in *Progress in Hemastasis and Thrombosis,* T. Spaet, ed., New York: A.R. Liss, pp. 167–182.
Maier et al., 1990, Science 249:1570–1574.
Maier et al., 1990, J. Biol. Chem. 265:10805–10808.
Martin–Zanca et al., 1989, Mol. Cell. Biol. 9:24–33.
Mello et al., 1994, Cell 77:95–106.
Melton, 1985, Proc. Natl. Acad. Sci. USA 82:144–148.
Montesano et al., 1986, Proc. Natl. Acad. Sci. USA 83:7297–7301.
Muskavitch 1994, Dev. Biology 166:415–430.
Muskavitch and Hoffmann, 1990, Curr. Top. Dev. Biol. 24:289–328.
Nishimura et al., 1987, Canc. Res. 47:999–1005.
Nye et al., 1994, Development 120:2421–2430.
Nye and Kopan, 1995, Curr. Biol. 5:966–969.
Okayama, 1983, Molec. Cell. Biol. 3:280–289.
Olander et al., 1985, J. Cell. Physiol. 125:1–9.
Pepper et al., 1992, Biochem. Biophys. Res. Comm. 189:824–831.
Preiss et al., 1985, Nature 313:27–32.
Prudovsky et al., 1994, J. Biol. Chem. 269:31720–31724.
Reaume et al., 1992, Dev. Biol. 154:377–387.
Reichman–Fried et al., 1994, Genes & Development 8:428–439.
Rosenberg et al., 1985, Nature 313:703–706.
Rosengart et al., 1989, Circ. Res. 64:227–234.
Rubin, 1988, Science 240:1453–1459.
Sasai et al., 1992, Genes Dev. 6:2620–2634.
Sato and Rifkin, 1988, J. Cell Biol. 107:1199–1205.
Scanlon et al., 1995, FASEB J. 9:1288–1296.
Schreiber et al., 1985, Proc. Natl. Acad. Sci. USA 82:6138–6142.
Schwartz et al., 1981, Atherosclerosis 1:107–161.
Schwartz et al., 1978, Lab. Invest. 38:568–580.
Schweisguth et al., 1992, Cell 69:1199–1212.
Seger and Krebs, 1995, The FASEB Journal 9:7216–735.
Setlow et al., eds. Plenum, 8:277–297.
Shaw et al., 1988, J. Natl.Cancer Inst. 80:1553–1559.
Silver et al., 1984, Proc. Natl. Acad. Sci. 81:5951–5955.
St. Groth et al., 1980, J. Immunol. Methods 35:1–21.
Sternberger et al., 1970, J. Histochem. Cytochem. 18:315–333.
Sun et al., 1987, Proc. Natl. Acad. Sci. USA 84:214–218.
Tax et al., 1994, Nature 368, 150–154.
Terranova et al., 1985, J. Cell Biol. 101:2330–2334.
Thomas et al., 1991, Development 111:749–761.
Ulmanen et al., 1985, J. Bacteriol. 162:176–182.
Ward et al., 1986, Mol. Gen. Genet. 203:468–478.
Weinmaster et al., 1991, Development 113:199–205.
Weinmaster et al., 1992, Development 116:931–941.
Weintraub, 1993, Cell 75:1241–1244.
Wood et al., 1985, Nature 314:446–449.
Zhan et al., 1994, J. Biol. Chem. 269:20221–20224.
Zhan et al., 1992, Biochem. Biophys. Res. Commun. 188:982–991.
Zimrin et al., 1995, Biochem. Biophys. Res. Commun. 213:630–638.
Zimrin et al., 1996, J. Clin. Invest. 97:1359.
*Johnstone, et al., 1987, Immun. Chemistry in Practice 30–47 .
*Zimrin et al., 1996, FASEB J. 10:A1094, Abstract No. 547.
*Zimrin et al., 1996, J. Biol. Chem. 271:32499–32502.
*Zubay 1984, In: Biochemistry; Bibliographies and Index: Biological chemistry.

* cited by examiner

Domain Structure of the Notch Ligand Family

- ▨ Intracellular Domain
- ■ Transmembrane Domain
- ⊠ Cys-Rich Domain
- ▯ EGF Repeat Domain
- ⫿ Delta Serrate Lag-2 (DSL) Domain
- ⊞ Signal Peptide Domain

Domain Structure of the Notch Receptor Family

- ■ Transmembrane Domain (T)
- ◻ Cys-Rich Domain (Notch Lin Glp Repeats, NLG)
- ☐ Ankyrin Repeat Domain
- ▨ Proline Glutamate Serine Threonine (PEST) Domain (A)
- ◳ Polyglutamine-Rich (OPA) Domain (O)
- ▤ Nuclear Localization Signal Domain (N)
- ⊠ Cys-Poor Domain (C)
- ⦀ EGF Repeat Domain
- ▯ Signal Peptide Sequence (S)

Jagged consensus Map (1 > 5458)  Site and Sequence    Settings:    Linear, Certain Sites Only, Standard Genetic Code

```
GGCACGAGCCTAAGCCTCGCCCTGCTCTGTGCCCTGCGAGCCAAGGTGTGTGGGGCCTCGGGTCAGTTCGAGTTGGAGATCCTGTCCAT
                                                                                      95
                 ─── signal peptide
         G  T  S  L  S  L  L  A  L  L  C  A  L  R  A  K  V  C  G  A  S  G  Q  F  E  L  E  I  L  S  M
GCAGAACGTGAACGGGAGCTGCAGAAGGAGTATCAGTCCCGCGTCACGGGAACTGTGCGGGCGCCCGGAACCCGGAGAGACCGGACGAGTGTGACACAT
                                                                                      190
   Q  N  V  N  G  E  L  Q  N  G  N  C  C  G  G  A  R  N  P  G  D  R  K  C  T  R  D  E  C  D  T ACTTCAAAGTGTGCCTCAAGGAGTATCAGTCCCGCGTCACGGCTTCGGCTCAGGTCTCACGCCTGTCATCGGGGCAAC
                                                                                      285
 Y  F  K  V  C  L  K  E  Y  Q  S  R  V  T  A  G  G  P  C  S  F  G  S  G  S  T  P  V  I  G  G  N ACCTTCAAACCTCAAGGCCAGCCGCGGCAACGACCGCAACCATCGTCGTGCCTGCCTGTGCCGAGGTCCTATACGTTGCTTGTGGA
                                                                                      380
   T  F  N  L  K  A  S  R  G  N  D  R  N  R  R  I  V  L  P  F  S  F  A  V  P  R  S  Y  T  L  L  V  E GGCGTGGGATTCCAGTAATGACACCGTTCAACCTGACAGTATTATTGAAAAGGCTTCTCACTCGGGCATGATCAACCCCAGCCGGCAGTGGCAGA
                                                                                      475
 A  W  D  S  S  N  D  T  V  Q  P  D  S;  I  I  E  K  A  S  H  S  G  M  I  N  P  S  R  Q  W  Q CGCTGAAGCAGAACACGGGCGTTGCCCACTTTGAGTATCAGATCCGCGTGATGACTACTACTATGGCTTTGGCTGCAATAAGTTCTGC
                                                                                      570
                                                  ─── DSL domain ───
   T  L  K  Q  N  T  G  V  A  H  F  E  Y  Q  I  R  V  T  C  D  D  Y  Y  Y  G  F  G  C  N  K  F  C
```

FIG.8A

CGCCCCAGAGATGACTTCTTTGGACACTATGCCTCTGTGACCAGAATGGCAACAAAACTTGCATGGAAGGCTGGATGGGCCCGAATGTAACAGAGC 665

R P R D D F F G H Y A C D Q N K T C M E G W M G P E C N R A

———————————— DSL domain ————————————

TATTTGCCGACAAGGCTGCAGTCCTAAGCATGGGTCTTGCAAACTCCCAGGTGACTGCAGGTGCCAGTATGGCTGGCAAGGCCTGTACTGTGATA 760

I C R Q G C S P K H G S C K L P G D C R C Q Y G W Q G L Y C D

———————————— EGF repeats ————————————

AGTGCATCCCACACCCGGGATGCGTCCACGGCATCTGTAATGAGCCCTGGCAGTGCCTCTGTGAGACCAACTGGGGCGGCCAGCTCTGTGACAAA 855

K C I P H P G C V H G I C N E P W Q C L C E T N W G G Q L C D K

———————————— EGF repeats ————————————

GATCTCAATTACTGTGGGACTCATCAGCCGTGTCTCAACGGGGAACTTGTAGCAACAGGCCCTGTCTCTGATCCCTGTCACAACAGAGGCAGCTGTAAGGAGACCTCCCTGGGG 950

D L N Y C G T H Q P C L N G G T C S N T G P D K Y Q C S C P E G

———————————— EGF repeats ————————————

GTATTCAGGACCCAACTGTGAAATTGCTGAGCACGCCTGCCTCTCTGATCCCTGTCACAACAGAGGCAGCTGTAAGGAGACCTCCCTGGGCTTTG 1045

Y S G P N C E I A E H A C L S D P C H N R G S C K E T S L G F

———————————— EGF repeats ————————————

```
CTCTGGAAACCTCTGTCAGCTGGACATCGATTATTGTGAGCCTAATCCCTGCCAGANCGGTGCCCAGTGCTACAACCGTGCCAGTGACTATTTCT                                    1615
                                                ———————EGF repeats———————
  S  G  N  L  C  Q  L  D  I  D  Y  C  E  P  N  P  C  Q  ?  G  A  Q  C  Y  N  R  A  S  D  Y  F
GCAAGTGCCCCGAGGACTATGAGGGCAAGAACTGCTCACACCTGAAAGACCACTGCCGCACGACCCCTGTGAAGTGATTGACAGCTGCACAGTG                                    1710
                                                                ———————EGF repeats———————
  C  K  C  P  E  D  Y  E  G  K  N  C  S  H  L  K  D  H  C  R  T  T  P  C  E  V  I  D  S  C  T  V
GCCATGGCTTCCAACGACACACCTGAAGGGGTGCGGTATATTTCCTCCAACGTCTGTGGTCCTCACGGAAGTGCAAGAGTCAGTGGGAGGCAA                                     1805
                                                                ———————EGF repeats———————
  A  M  A  S  N  D  T  P  E  G  V  R  Y  I  S  S  N  V  C  G  P  H  G  K  C  K  S  Q  G  G  K
ATTCACCTGTGACTGTAACAAAGGCTTCACGGGAACATACTGCCATGAGAATATTAATGACTGTGAGAGCAACCCTTGTAGAAACGGTGGCACTT                                   1900
                                                                ———————EGF repeats———————
  F  T  C  D  C  N  K  G  F  T  G  T  Y  C  H  E  N  I  N  D  C  E  S  N  P  C  R  N  G  G  T
GCATCGATGGTGTCAACTCCTACAAGTGCATCTGTAGTGACGGCTGGGAGGGGCCTACTGTGAAACCAATATTAATGACTGCAGCCAGAACCCC                                    1995
                                                                ———————EGF repeats———————
  C  I  D  G  V  N  S  Y  K  C  I  C  S  D  G  W  E  G  A  Y  C  E  T  N  I  N  D  C  S  Q  N  P
```

FIG. 8D

TGCCACAATGGGGGCACGTGTCGCGACCTGGTCAATGACTTCTACTGTGACTGTAAAAATGGGTGGAAAGGAAAGACCTGCCACTCACGTGACAG 2090

———— EGF repeats ————

C H N G G T C R D L V N D F Y C D C K N G W K G K T C H S R D S

TCAGTGTGATGAGGCCACGTGCAACAACGGTGGCACCTGCTATGATGAGGGGGATGCTTTTAAGTGCATGTGTCCTGGCGGTGTGGGAAGGAACAA 2185

———— EGF repeats ————

Q C D E A T C N N G G T C Y D E G D A F K C M C P G G V E G T

CCTGTAACATAGCCCGAAACAGTAGCCTGCCTAACCCCTGCCATAATGGGGGCACATGTGTGGTCAACGGCGAGTCCTTTACGTGCGTCTGC 2280

———— EGF repeats ————

T C N I A R N S S C L P N P C H N G G T C V V N G E S F T C V C

AAGGAAGGCTGGGAGGGGCCCATCTGTGCTCAGAATACCAATGACTGCAGCCCTCATCCCTGTTACAACAGCGGCACCTGTGTGGATGGAGACAA 2375

———— EGF repeats ————

K E G W E G P I C A Q N T N D C S P H P C Y N S G T C V D G D N

CTGGTACCGGTGCGAATGTGCCCCGGGTTTTGCTGGGCCCGACTGCAGAATAAACATCAATGAATGCCAGTCTTCACCTTGTGCCTTTGGAGCGA 2470

———— EGF repeats ————

CCTGTGTGGATGAGATCAATGGCTACCGGTGTGTCTGCCCTCCAGGGCACAGTGGTGCCAAGTGCCAGGAAGTTTCAGGGAGACCTTGCATCACC 2565
————————————————————————————————————————————————— EGF repeats ————————————————————————————————————→ | cysteine-r-
T C V D E I N G Y R C V C P P G H S G A K C Q E V S G R P C I T ATGGGGAGTGTGATACCAGATGGGGCCAAATGGGACGATGACGATAATACCCAGTGCCTGAATGGACGGATCGCCTGCTCAAAGGTCTGGTG 2660
———————————————————————————————————————————————— cysteine-rich region ————————————————————————————————————
M G S V I P D G A K W D D D C N T C Q C L N G R I A C S K V W C TGGCCCCTGACCTTGCCTGCTCCACACAAAGGGCACAGCGAGTGCCCCAGCGGGCAGTCTTGCATCCCCATCCTGACTCCCATCCTATTACCAGGATAACTGTGCGAAC 2755
———————————————————————————————————————————————— cysteine-rich region ————————————————————————————————————
G P R P C L L H K G H S E C P S G Q S C I P I L D Q Q C F V H CCTGCACTGGTGTGGGCGAGTGTCGGTCTTCCAGTCTCCAGCGGTGAAGACAAAGTGCACCTTGACTCCTATTACCAGGATAACTGTGCGAAC 2850
———————————————————————————————————————————————— cysteine-rich region ————————————————————————————————————
G P T G V G E C R S S L Q P V K T K C T S D S Y Y Q D N C A N ATCACATTTACCTTTAACAAGGAGATGATGTCACCAGGTCTTACTACGGAGCACATTTGCAGTGAATTGAGGAATTTGAATATTTGAAGAATGT 2945
———————————————————————————————————————————————— cysteine-rich region ————————————————————————————————————
I T F T F N K E M M S P G L T T E H I C S E L R N L N I L K N V

FIG.8F

```
TTCCGCTGAATATTCAATCTACATCGCTTGCCCCTTCAGCGAACAATGAAATACATGTGGCCATTTCTGCTGAAGATATACGGGATG   3040
       S  A  E  Y  S  I  Y  I  A  C  E  P  S  P  S  A  N  N  E  I  H  V  A  I  S  A  E  D  I  R  D
                 |———— cysteine-rich region ————

ATGGGAACCCGATCAAGGAAATCACTGACAAATAATCGATCTTGTTAGTAAACGTGATGGAAACAGCTCGCTGATTGCTGCCGTTGCAGAAGTA   3135
  D  G  N  P  I  K  E  I  T  D  K  I  I  D  L  V  S  K  R  D  G  N  S  S  L  I  A  A  V  A  E  V

AGAGTTCAGAGAGGCGGCCTCTGAAGAACAGAGAAACAGATTTCCTTGTTCCTTGCTTAGTGTCCTGTCTGTCTTAACTGTGGCTTGTTGCTTGGTGAC   3230
  R  V  Q  R  R  P  L  K  N  R  T  D  F  L  V  P  L  L  S  S  V  L  T  V  A  W  I  C  C  L  V  T
                                              |———————— transmembrane domain GGCCTTCTACTGGTGCCTGCGGAAGCGGGCAGCCAACACTCAGCCTCTGAGGACAACAACAACGTGCGGGAGCAGC   3325
  A  F  Y  W  C  L  R  K  R  R  K  P  G  S  H  T  H  S  A  E  D  N  T  T  N  N  V  R  E  Q
————| |———————— cytoplasmic region
 transmembrane domain TGAACCAGATCAAAAACCCCATTGAGAAACATGGGGCCAACACGGTCCCCATCAAGGATTACGAGAACAAGAACTCCAAAATGTCTAAAATAAGG   3420
  L  N  Q  I  K  N  P  I  E  K  H  G  A  N  T  V  P  I  K  D  Y  E  N  K  N  S  K  M  S  K  I  R
                           ———————— cytoplasmic region
```

FIG.8G

```
ACACACAATTCTGAAGTAGAGAGGAGGACGACATGGACAAACACCAGCAGAAAGCCCGGTTTTGCTTGGCAAGCAGCCCGGCGTTTTCGCTGGTAGACAGAGA
                                                                                                    ─ 3515
                          ┌──────────────────── cytoplasmic region ──────────
 T  H  N  S  E  V  E  E  D  D  M  D  K  H  Q  Q  K  A  R  F  G  K  Q  P  A  F  S  L  V  D  R  E
AGAGAAGCCCCCCAACGGCACGCCGACGCCGAAACTGGACAAACACCCAAACTGGACAAACAAACAGAGGACAACAGAGACTTGGAAAGTGCCCAGAGCTTAAACCGAA
                                                                                                    ─ 3610
────────────────────── cytoplasmic region ──────────
 E  K  P  P  N  G  T  P  T  K  H  P  N  W  T  N  K  Q  D  N  R  D  L  E  S  A  Q  S  L  N  R
TGGAGTACATCGTATAGCAGACCGCGGGCACTGCCGCCGCCTAGGTAGAGTCTGAGGGCTTGTAGTTCTTAAACTGTCGTGTCATACTCGAGTCT
                                                                                                    ─ 3705
  ↑ cytoplasmic region
 M  E  Y  I  V
GAGGCCGTTGCTGACTTAGAATCCCTGTGTTAATTTAAGTTTTGACAAGCTGGCTTACACTGGCAATGGTAGTTTCTGKGGTTGGCTGGGAAATC
                                                                                                    ─ 3800
GAGTGCCGCATCTCACAGCTAGTCAACAGTACCCTGGTTGTGTCCCCTTGCCAGCCGACACGGTCTCGGATCAGGCTCCCAG
                                                                                                    ─ 3895
GAGCCTGCCCAGCCCCCCTGGTCTCTTTGAGCTCCCACTTCTGCCAGATGTCCTAATGGTGATGCAGTCTTAGATCATAGTTTATTTATATTTATTG
                                                                                                    ─ 3990
ACTCTTGAGTTGTTTTTGTATATTGGTTTTTATGATGACGNACAAGTAGTTCTGTATTTGAAAGTGCCTTTGCAGCTCAGAACCACAGCAACGATC
                                                                                                    ─ 4085
```

FIG.8H

```
ACAAATGACTTTATTATTTTTAATTGTATTTTTGTGTTGGGGAGGGGAGACTTTGATGTCAGCAGTTGCTGGTAAAATGAAGAATTT    4180

AAAGAARAAAAATGTCMMMNAGTAGAACTTTGTATAGTTATGTAAATAATTCTTTTTTATTAATCACTGTGTATATTTGATTAKATTAAMTTAATA    4275

ATCAAGAGCCTTAAAAACATCATTCCTTTTATTTATATGTATGTGTTAGAATTGNAGGTTTTTGATAGCATTGTAAGCGTATGGCTTTATTTTT    4370

TTGAACTCTTCTCATTACTTGTTGCCTATAAGCCMMMATTAAGGTGTTTGAAAATAGTTTATTTTAAAACAATAGGATGGGCTTCTGTGCCAGA    4465

ATACTGATGGAATTTTTTTGTACGACGTCAGATGTTTAAAACACCTTCTATAGCATCACTTAAAACACGTTTAAGGACTGACTGAGGCAGTTT    4560

GAGGATTAGTTTAGAACAGGTTTTTTTGTTTTGTTTTTTGTTTTTCTGCCTTTAGACTTGAAAAGAGACAGGCAGGTGATCTGCTGCAGAGCA    4655

GTAAGGGAACAAGTTGAGCTATGACTTAACATAGCCAAAATGTGAGTGGTTGAATATGATTAAAAATATCAAATTAATTGTGTGAACTTGGAAGC    4750

ACACCAATCTGACTTGTAAATTCTGATTTCTTTTCACCATTCGTACATAATACTGAACCACTTGTAGATTTGATTTTTTTTTTAATCTACTGCA    4845

TTTAGGGAGTATTCTAATAAGCTAGTTGAATACTTGAACCATAAAAATGTCCAGTAAGATCACTGTTTAGATTTGCCATAGAGTACACTGCCTGCC    4940

TTAAGTGAGGAAATCAAAGTGCTATTACGAAGTTCAAGATCNAAAAGGCTTATAAAAACAGAGTAATCTTGTGGTTCACCATTGAGACCGTGAAG    5035
```

FIG. 8I

```
ATACTTTGTATTGTCCTATTAGTGTTATATGAACABACAAATGCATCTTTGATGTGTTGTTCTTGGCAATAAATTTGAAAAGTAATATTTATTA  5130

AATTTTTTGTATGAAAACATGGAACAGTGTGGCCCTCTTCTTCTGAGCTTACGTAGTTCTACCGGCTTTGCCGTGTGCTTCTGCCACCCTGCTGAGTC  5225

TGTTCTGGTAATCGGGGTATAATAGGCTCTGCCTGACAGAGAGGGATGGAGGAAGAACTGAAAGGCTTTTCAACCACAAAACTCATCTGGAGTTCTC  5320

AAAGACCTGGGGCTGCTGTGAAGCTGGAACTGCGGGAGCCCCATCTAGGGGAGCCTTGATTCCCTTGTTATTCAACAGCAAGTGTGAATACTGCT  5415

TGAATAAACACCACTGGATTAAAAAAAAAAAAAAAAGGCA
```

FIG.8J

SEQUENCE LISTING

<160> NUMBER OF SEQ ID NOS: 16

<210> SEQ ID NO 1
<211> LENGTH: 1208
<212> TYPE: PRT
<213> ORGANISM: Homo sapiens

<400> SEQUENCE: 1

```
Gly Thr Ser Leu Ser Leu Leu Leu Ala Leu Leu Cys Ala Leu Arg Ala
 1               5                  10                  15

Lys Val Cys Gly Ala Ser Gly Gln Phe Glu Leu Glu Ile Leu Ser Met
            20                  25                  30

Gln Asn Val Asn Gly Glu Leu Gln Asn Gly Asn Cys Cys Gly Gly Ala
        35                  40                  45

Arg Asn Pro Gly Asp Arg Lys Cys Thr Arg Asp Glu Cys Asp Thr Tyr
    50                  55                  60

Phe Lys Val Cys Leu Lys Glu Tyr Gln Ser Arg Val Thr Ala Gly Gly
65                  70                  75                  80

Pro Cys Ser Phe Gly Ser Gly Ser Thr Pro Val Ile Gly Gly Asn Thr
                85                  90                  95

Phe Asn Leu Lys Ala Ser Arg Gly Asn Asp Pro Asn Arg Ile Val Leu
            100                 105                 110

Pro Phe Ser Phe Ala Trp Pro Arg Ser Tyr Thr Leu Leu Val Glu Ala
        115                 120                 125

Trp Asp Ser Ser Asn Asp Thr Val Gln Pro Asp Ser Ile Ile Glu Lys
    130                 135                 140

Ala Ser His Ser Gly Met Ile Asn Pro Ser Arg Gln Trp Gln Thr Leu
145                 150                 155                 160

Lys Gln Asn Thr Gly Val Ala His Phe Glu Tyr Gln Ile Arg Val Thr
```

-continued

```
                165                 170                 175
Cys Asp Asp Tyr Tyr Gly Phe Gly Cys Asn Lys Phe Cys Arg Pro
            180                 185                 190
Arg Asp Asp Phe Phe Gly His Tyr Ala Cys Asp Gln Asn Gly Asn Lys
            195                 200                 205
Thr Cys Met Glu Gly Trp Met Gly Pro Glu Cys Asn Arg Ala Ile Cys
            210                 215                 220
Arg Gln Gly Cys Ser Pro Lys His Gly Ser Cys Lys Leu Pro Gly Asp
225                 230                 235                 240
Cys Arg Cys Gln Tyr Gly Trp Gln Gly Leu Tyr Cys Asp Lys Cys Ile
                245                 250                 255
Pro His Pro Gly Cys Val His Gly Ile Cys Asn Glu Pro Trp Gln Cys
                260                 265                 270
Leu Cys Glu Thr Asn Trp Gly Gly Gln Leu Cys Asp Lys Asp Leu Asn
                275                 280                 285
Tyr Cys Gly Thr His Gln Pro Cys Leu Asn Gly Gly Thr Cys Ser Asn
            290                 295                 300
Thr Gly Pro Asp Lys Tyr Gln Cys Ser Cys Pro Glu Gly Tyr Ser Gly
305                 310                 315                 320
Pro Asn Cys Glu Ile Ala Glu His Ala Cys Leu Ser Asp Pro Cys His
                325                 330                 335
Asn Arg Gly Ser Cys Lys Glu Thr Ser Leu Gly Phe Glu Cys Glu Cys
                340                 345                 350
Ser Pro Gly Trp Thr Gly Pro Thr Cys Ser Thr Asn Ile Asp Asp Cys
                355                 360                 365
Ser Pro Asn Asn Cys Ser His Gly Gly Thr Cys Gln Asp Leu Val Asn
            370                 375                 380
Gly Phe Lys Cys Val Cys Pro Pro Gln Trp Thr Gly Lys Thr Cys Gln
385                 390                 395                 400
Leu Asp Ala Asn Glu Cys Glu Ala Lys Pro Cys Val Asn Ala Lys Ser
                405                 410                 415
Cys Lys Asn Leu Ile Ala Ser Tyr Tyr Cys Asp Cys Leu Pro Gly Trp
                420                 425                 430
Met Gly Gln Asn Cys Asp Ile Asn Ile Asn Asp Cys Leu Gly Gln Cys
                435                 440                 445
Gln Asn Asp Ala Ser Cys Arg Asp Leu Val Asn Gly Tyr Arg Cys Ile
            450                 455                 460
Cys Pro Pro Gly Tyr Ala Gly Asp His Cys Glu Arg Asp Ile Asp Glu
465                 470                 475                 480
Cys Ala Ser Asn Pro Cys Leu Asn Gly Gly His Cys Gln Asn Glu Ile
                485                 490                 495
Asn Arg Phe Gln Cys Leu Cys Pro Thr Gly Phe Ser Gly Asn Leu Cys
                500                 505                 510
Gln Leu Asp Ile Asp Tyr Cys Glu Pro Asn Pro Cys Gln Asn Gly Ala
            515                 520                 525
Gln Cys Tyr Asn Arg Ala Ser Asp Tyr Phe Cys Lys Cys Pro Glu Asp
            530                 535                 540
Tyr Glu Gly Lys Asn Cys Ser His Leu Lys Asp His Cys Arg Thr Thr
545                 550                 555                 560
Pro Cys Glu Val Ile Asp Ser Cys Thr Val Ala Met Ala Ser Asn Asp
                565                 570                 575
Thr Pro Glu Gly Val Arg Tyr Ile Ser Ser Asn Val Cys Gly Pro His
                580                 585                 590
```

-continued

```
Gly Lys Cys Lys Ser Gln Ser Gly Lys Phe Thr Cys Asp Cys Asn
            595                 600                 605
Lys Gly Phe Thr Gly Thr Tyr Cys His Glu Asn Ile Asn Asp Cys Glu
    610                 615                 620
Ser Asn Pro Cys Arg Asn Gly Thr Cys Ile Asp Gly Val Asn Ser
625                 630                 635                 640
Tyr Lys Cys Ile Cys Ser Asp Gly Trp Glu Gly Ala Tyr Cys Glu Thr
                645                 650                 655
Asn Ile Asn Asp Cys Ser Gln Asn Pro Cys His Asn Gly Gly Thr Cys
            660                 665                 670
Arg Asp Leu Val Asn Asp Phe Tyr Cys Asp Cys Lys Asn Gly Trp Lys
        675                 680                 685
Gly Lys Thr Cys His Ser Arg Asp Ser Gln Cys Asp Glu Ala Thr Cys
    690                 695                 700
Asn Asn Gly Gly Thr Cys Tyr Asp Glu Gly Asp Ala Phe Lys Cys Met
705                 710                 715                 720
Cys Pro Gly Gly Trp Glu Gly Thr Thr Cys Asn Ile Ala Arg Asn Ser
                725                 730                 735
Ser Cys Leu Pro Asn Pro Cys His Asn Gly Gly Thr Cys Val Val Asn
            740                 745                 750
Gly Glu Ser Phe Thr Cys Val Cys Lys Glu Gly Trp Glu Gly Pro Ile
        755                 760                 765
Cys Ala Gln Asn Thr Asn Asp Cys Ser Pro His Pro Cys Tyr Asn Ser
    770                 775                 780
Gly Thr Cys Val Asp Gly Asp Asn Trp Tyr Arg Cys Glu Cys Ala Pro
785                 790                 795                 800
Gly Phe Ala Gly Pro Asp Cys Arg Ile Asn Ile Asn Glu Cys Gln Ser
                805                 810                 815
Ser Pro Cys Ala Phe Gly Ala Thr Cys Val Asp Glu Ile Asn Gly Tyr
            820                 825                 830
Arg Cys Val Cys Pro Pro Gly His Ser Gly Ala Lys Cys Gln Glu Val
        835                 840                 845
Ser Gly Arg Pro Cys Ile Thr Met Gly Ser Val Ile Pro Asp Gly Ala
    850                 855                 860
Lys Trp Asp Asp Asp Cys Asn Thr Cys Gln Cys Leu Asn Gly Arg Ile
865                 870                 875                 880
Ala Cys Ser Lys Val Trp Cys Gly Pro Arg Pro Cys Leu Leu His Lys
                885                 890                 895
Gly His Ser Glu Cys Pro Ser Gly Gln Ser Cys Ile Pro Ile Leu Asp
            900                 905                 910
Asp Gln Cys Phe Val His Pro Cys Thr Gly Val Gly Glu Cys Arg Ser
        915                 920                 925
Ser Ser Leu Gln Pro Val Lys Thr Lys Cys Thr Ser Asp Ser Tyr Tyr
    930                 935                 940
Gln Asp Asn Cys Ala Asn Ile Thr Phe Thr Phe Asn Lys Glu Met Met
945                 950                 955                 960
Ser Pro Gly Leu Thr Thr Glu His Ile Cys Ser Glu Leu Arg Asn Leu
                965                 970                 975
Asn Ile Leu Lys Asn Val Ser Ala Glu Tyr Ser Ile Tyr Ile Ala Cys
            980                 985                 990
Glu Pro Ser Pro Ser Ala Asn Asn Glu Ile His Val Ala Ile Ser Ala
        995                 1000                1005
```

```
Glu Asp Ile Arg Asp Asp Gly Asn Pro Ile Lys Glu Ile Thr Asp Lys
    1010                1015                1020

Ile Ile Asp Leu Val Ser Lys Arg Asp Gly Asn Ser Ser Leu Ile Ala
1025                1030                1035                1040

Ala Val Ala Glu Val Arg Val Gln Arg Arg Pro Leu Lys Asn Arg Thr
                1045                1050                1055

Asp Phe Leu Val Pro Leu Leu Ser Ser Val Leu Thr Val Ala Trp Ile
            1060                1065                1070

Cys Cys Leu Val Thr Ala Phe Tyr Trp Cys Leu Arg Lys Arg Arg Lys
        1075                1080                1085

Pro Gly Ser His Thr His Ser Ala Ser Glu Asp Asn Thr Thr Asn Asn
    1090                1095                1100

Val Arg Glu Gln Leu Asn Gln Ile Lys Asn Pro Ile Glu Lys His Gly
1105                1110                1115                1120

Ala Asn Thr Val Pro Ile Lys Asp Tyr Glu Asn Lys Asn Ser Lys Met
                1125                1130                1135

Ser Lys Ile Arg Thr His Asn Ser Glu Val Glu Glu Asp Asp Met Asp
            1140                1145                1150

Lys His Gln Gln Lys Ala Arg Phe Ala Lys Gln Pro Ala Tyr Thr Leu
        1155                1160                1165

Val Asp Arg Glu Glu Lys Pro Pro Asn Gly Thr Pro Thr Lys His Pro
    1170                1175                1180

Asn Trp Thr Asn Lys Gln Asp Asn Arg Asp Leu Glu Ser Ala Gln Ser
1185                1190                1195                1200

Leu Asn Arg Met Glu Tyr Ile Val
            1205

<210> SEQ ID NO 2
<211> LENGTH: 5458
<212> TYPE: DNA
<213> ORGANISM: Homo sapiens

<400> SEQUENCE: 2
ggcacgagcc taagcctcct gctcgccctg ctctgtgccc tgcgagccaa ggtgtgtggg      60
gcctcgggtc agttcgagtt ggagatcctg tccatgcaga acgtgaacgg ggagctgcag     120
aacgggaact gctgcggcgg cgcccggaac ccgggagacc gcaagtgcac ccgcgacgag     180
tgtgacacat acttcaaagt gtgcctcaag gagtatcagt cccgcgtcac ggccgggggg     240
ccctgcagct tcggctcagg gtccacgcct gtcatcgggg caacaccttt caacctcaag     300
gccagccgcg gcaacgaccc gaaccgcatc gtgctgcctt tcagtttcgc ctggccgagg     360
tcctatacgt tgcttgtgga ggcgtgggat tccagtaatg acaccgttca acctgacagt     420
attattgaaa aggcttctca ctcgggcatg atcaacccca gccggcagtg gcagacgctg     480
aagcagaaca cgggcgttgc ccactttgag tatcagatcc gcgtgacctg tgatgactac     540
tactatggct ttggctgtaa taagttctgc cgccccagag atgacttctt tggacactat     600
gcctgtgacc agaatggcaa caaaacttgc atggaaggct ggatgggccc cgaatgtaac     660
agagctattt gccgacaagg ctgcagtcct aagcatgggt cttgcaaact cccaggtgac     720
tgcaggtgcc agtacggctg gcaaggcctt actgtgata agtgcatccc acacccggga     780
tgcgtccacg gcatctgtaa tgagccctgg cagtgcctct gtgagaccaa ctgggcggc      840 cagctctgtg acaaagatct caattactgt gggactcatc agccgtgtct caacggggga     900
acttgtagca cacaggcccc tgacaaatat cagtgttcct gccctgaggg gtattcagga     960
```

-continued

```
cccaactgtg aaattgctga gcacgcctgc ctctctgatc cctgtcacaa cagaggcagc    1020
tgtaaggaga cctccctggg ctttgagtgt gagtgttccc caggctggac cggccccaca    1080
tgctctacaa acattgatga ctgttctcct aataactgtt cccacggggg cacctgccag    1140
gacctggtta acggatttaa gtgtgtgtgc cccccacagt ggactgggaa aacgtgccag    1200
ttagatgcaa atgaatgtga ggccaaacct tgtgtaaacg ccaaatcctg taagaatctc    1260
attgccagct actactgcga ctgtcttccc ggctggatgg gtcagaattg tgacataaat    1320
attaatgact gccttggcca gtgtcagaat gacgcctcct gtcgggattt ggttaatggt    1380
tatcgctgta tctgtccacc tggctatgca ggcgatcact gtgagagaga catcgatgaa    1440
tgtgccagca cccctgtttt gaatgggggt cactgtcaga atgaaatcaa cagattccag    1500
tgtctgtgtc ccactggttt ctctggaaac tctgtcagc tggacatcga ttattgtgag    1560
cctaatccct gccagaacgg tgcccagtgc acaaccgtg ccagtgacta tttctgcaag    1620
tgccccgagg actatgaggg caagaactgc tcacacctga agaccactg ccgcacgacc    1680 ccctgtgaag tgattgacag ctgcacagtg gccatggctt ccaacgacac acctgaaggg    1740
gtgcggtata tttcctccaa cgtctgtggt cctcacggga agtgcaagag tcagtcggga    1800
ggcaaattca cctgtgactg taacaaaggc ttcacgggaa catactgcca tgaaaatatt    1860
aatgactgtg agagcaaccc ttgtagaaac ggtggcactt gcatcgatgg tgtcaactcc    1920
tacaagtgca tctgtagtga cggctgggag ggggcctact gtgaaaccaa tattaatgac    1980
tgcagccaga ccctgccaa atgggggc acgtgtcgcg acctggtcaa tgacttctac    2040
tgtgactgta aaaatgggtg gaaggaaag acctgccact cacgtgacag tcagtgtgat    2100
gaggccacgt gcaacaacgg tggcacctgc tatgatgagg gggatgcttt taagtgcatg    2160
tgtcctggcg gctgggaagg aacaacctgt aacatagccc gaaacagtag ctgcctgccc    2220 aaccctgcc ataatggggg cacatgtgtg gtcaacggcg agtcctttac gtgcgtctgc    2280
aaggaaggct gggagggcc catctgtgct cagaatacca atgactgcag ccctcatccc    2340
tgttacaaca gcggcacctg tgtggatgga gacaactggt accggtgcga atgtgccccg    2400
ggttttgctg ggcccgactg cagaataaac atcaatgaat gccagtcttc accttgtgcc    2460 tttgagcga cctgtgtgga tgagatcaat ggctaccggt gtgtctgccc tccagggcac    2520
agtggtgcca agtgccagga gtttcaggg agaccttgca tcaccatggg gagtgtgata    2580
ccagatgggg ccaaatggga tgatgactgt aatacctgcc agtgcctgaa tggacggatc    2640
gcctgctcaa aggtctggtg tggccctcga ccttgcctgc tccacaaagg gcacagcgag    2700
tgccccagcg ggcagagctg catccccatc ctggacgacc agtgcttcgt ccaccctgc    2760 actggtgtgg gcgagtgtcg gtcttccagt ctccagccgg tgaagacaaa gtgcacctct    2820
gactcctatt accaggataa ctgtgcgaac atcacattta cctttaacaa ggagatgatg    2880
tcaccaggtc ttactacgga gcacatttgc agtgaattga ggaattgaa tattttgaag    2940 aatgtttccg ctgaatattc aatctacatc gcttgcgagc cttcccctcc agcgaacaat    3000
gaaatacatg tggccatttc tgctgaagat atacgggatg atgggaaccc gatcaaggaa    3060
atcactgaca aaataatcga tcttgttagt aaacgtgatg gaaacagctc gctgattgct    3120
gccgttgcag aagtaagagt tcagaggcgg cctctgaaga acagaacaga tttccttgtt    3180
cccttgctga gctctgtctt aactgtggct tggatctgtt gcttggtgac ggccttctac    3240
tggtgcctgc ggaagcggcg gaagccgggc agccacacac actcagcctc tgaggacaac    3300
accaccaaca acgtgcggga gcagctgaac cagatcaaaa accccattga gaacatgggg    3360
```

-continued

```
gccaacacgg tccccatcaa ggattacgag aacaagaact ccaaaatgtc taaaataagg    3420
acacacaatt ctgaagtaga agaggacgac atggacaaac accagcagaa agcccggttt    3480
gccaagcagc cggcgtacac gctggtagac agagaagaga agcccccaa cggcacgccg    3540 acaaaacacc caaactggac aaacaaacag acaacagag acttggaaag tgcccagagc    3600
ttaaaccgaa tggagtacat cgtatagcag accgcgggca ctgccgccgc taggtagagt    3660
ctgagggctt gtagttcttt aaactgtcgt gtcatactcg agtctgaggc cgttgctgac    3720
ttagaatccc tgtgttaatt tagtttgaca agctggctta cactggcaat ggtagttctg    3780
tggttggctg ggaaatcgag tggcgcatct cacagctatg caaaaagcta gtcaacagta    3840
cccctggttg tgtgtcccct tgcagccgac acggtctcgg atcaggctcc caggagctgc    3900
ccagccccct ggtactttga gctcccactt ctgccagatg tctaatggtg atgcagtctt    3960
agatcatagt tttatttata tttattgact cttgagttgt ttttgtatat tggttttatg    4020
atgacgtaca agtagttctg tatttgaaag tgcctttgca gctcagaacc acagcaacga    4080
tcacaaatga ctttattatt tatttttttt aattgtattt tgttgttgg gggaggggag    4140 actttgatgt cagcagttgc tggtaaaatg aagaatttaa agaaaaatg tccaaaagta    4200 gaactttgta tagttatgta ataattctt tttattaat cactgtgtat atttgattta    4260
ttaacttaat aatcaagagc cttaaaacat cattccttt tatttatatg tatgtgttta    4320
gaattgaagg tttttgatag cattgtaagc gtatggcttt attttttga actcttctca    4380 ttacttgttg cctataagcc aaaaaggaaa gggtgttttg aaaatagttt attttaaaac    4440
aataggatgg gcttctgtgc ccagaatact gatggaattt ttttgtacg acgtcagatg    4500 tttaaaacac cttctatagc atcacttaaa acacgtttta aggactgact gaggcagttt    4560
gaggattagt ttagaacagg ttttttgtt tgtttgtttt tgtttttct gctttagact    4620 tgaaaagaga caggcaggtg atctgctgca gagcagtaag ggaacaagtt gagctatgac    4680
ttaacatagc caaatgtga gtggttgaat atgattaaaa atatcaaatt aattgtgtga    4740
acttggaagc acaccaatct gactttgtaa attctgattt cttttcacca ttcgtacata    4800
atactgaacc acttgtagat ttgattttt ttttaatcta ctgcatttag ggagtattct    4860
aataagctag ttgaatactt gaaccataaa atgtccagta agatcactgt ttagatttgc    4920
catagagtac actgcctgcc ttaagtgagg aaatcaaagt gctattacga agttcaagat    4980
cmaaaaggct tataaaacag agtaatcttg ttggttcacc attgagaccg tgaagatact    5040
ttgtattgtc ctattagtgt tatatgaaca bacaaatgca tctttgatgt gttgttcttg    5100
gcaataaatt ttgaaaagta atatttatta aattttttg tatgaaaaca tggaacagtg    5160
tggcctcttc tgagcttacg tagttctacc ggctttgccg tgtgcttctg ccaccctgct    5220
gagtctgttc tggtaatcgg ggtataatag gctctgcctg acagagggat ggaggaagaa    5280
ctgaaaggct tttcaaccac aaaactcatc tggagttctc aaagacctgg ggctgctgtg    5340
aagctggaac tgcgggagcc ccatctaggg gagccttgat tcccttgtta ttcaacagca    5400
agtgtgaata ctgcttgaat aaacaccact ggattaaaaa aaaaaaaaa aaaaggca     5458
```

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: 3' reverse
      transcription primer -continued

```
<400> SEQUENCE: 3
gcgcaagctt tttttttttt cg                                          22

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: cDNA
      amplification 5'-primer

<400> SEQUENCE: 4
gagaccgtga agatactt                                               18

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Jagged
      sense
      primer

<400> SEQUENCE: 5
ccgactgcag aataaacatc                                             20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Jagged
      antisense primer

<400> SEQUENCE: 6
ttggatctgg ttcagctgct                                             20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Notch 1
      sense primer

<400> SEQUENCE: 7
ttcagtgacg gccactgtga                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Notch 1
      antisense primer

<400> SEQUENCE: 8
cacgtacatg aagtgcagct                                             20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Notch 2
      sense primer
```

```
<400> SEQUENCE: 9
tgagtaggct ccatccagtc                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Notch 2
      antisense primer

<400> SEQUENCE: 10
tggtgtcagg tagggatgct                                               20

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: GAPDH
      sense primer

<400> SEQUENCE: 11
ccacccatgg caaattccat ggca                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: GAPDH
      antisense primer

<400> SEQUENCE: 12
tctagacggc aggtcaggtc cacc                                          24

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: 5' end
      Myc tag construction: sense primer

<400> SEQUENCE: 13
gactatgcga attcggatcc gtcgacgcca ccatgg                             36

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:  5' end Myc
      tag construction: antisense primer

<400> SEQUENCE: 14
caagttcccc cgttgagaca                                               20

<210> SEQ ID NO 15
<211> LENGTH: 65
<212> TYPE: DNA
<213> ORGANISM: Artificial Sequence
<220> FEATURE:
<223> OTHER INFORMATION: Description of Artificial Sequence:  3' end Myc
      tag construction: antisense primer
```

-continued

```
<400> SEQUENCE: 15
gcatagtcct cgagttacaa gtcttcttca gaaataagct tttgttctac gatgtactcc      60
attcg                                                                 65

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:  3' end Myc
      tag construction: sense primer

<400> SEQUENCE: 16
atggacaaac accagcagaa                                                 20
```

THERAPEUTIC AND DIAGNOSTIC METHODS AND COMPOSITIONS BASED ON JAGGED/NOTCH PROTEINS AND NUCLEIC ACIDS

CROSS-REFERENCE TO RELATED APPLICATIONS

This application is a Division of U.S. patent application Ser. No. 09/199,865, filed Nov. 25, 1998, now issued as U.S. Patent No. 6,433,138, which is a Continuation of International Application No. PCT/US97/09407, filed May 30, 1997, all of which are entitled to priority under 35 U.S.C. § 119(e) to U.S. Provisional Application No. 60/018,841, filed on May 31, 1996, and all of which are hereby incorporated herein by reference in their entirety.

STATEMENT OF GOVERNMENT RIGHTS IN THE INVENTION

Part of the work performed during the development of this invention utilized U.S. Government funds and NIH grants. Thus, the U.S. Government may have certain rights in the invention.

BACKGROUND OF THE INVENTION

1. Field of the Invention

The present invention relates to therapeutic and diagnostic methods and compositions based on Jagged/Notch proteins and nucleic acids, and on the role of their signaling pathway in endothelial cell migration and/or differentiation.

2. Background of the Invention

The functional integrity of the human vascular system is maintained by the endothelial cell which monitors the non-thrombogenic interface between blood and tissue in vivo. Thus, factors that influence human endothelial cell function may contribute significantly to the regulation and maintenance of homeostasis (see, Maciag, in *Progress in Hemostasis and Thrombosis*, T. Spaet, ed. (New York: A. R. Liss), pp.167–182 (1984); Folkman and Klagsbum, *Science* 235:442–447 (1987); Burgess and Maciag, *Annu. Rev. Biochen.* 58:575–606 (1989)). Likewise, events that perturb this complex equilibrium are relevant to the pathophysiology of human disease states in which cellular components of the vascular tree are active participants including, e.g., atherogenesis, coronary insufficiency, hypertension, rheumatoid arthritis, solid tumor growth and metastasis, and wound repair.

Since the endothelium is present in all organs and tissues, endothelial cell function is also fundamental to the physiology and integration of these multicellular systems. This includes the ability to monitor and interface with repair systems that employ the tightly regulated inflammatory, angiogenic and neurotropic responses. Indeed, biochemical signals that are responsible for the modification of these responses have been well characterized as polypeptide growth factors and cytokines; however, their mechanisms of operation have, prior to the present invention, been poorly understood, impeding their acceptance as valuable tools in clinical management.

A major accomplishment of modern biology has been the recognition that structural elements responsible for physiologic functions are conserved throughout the animal kingdom. Genetic analysis of yeast, *C. elegans*, Xenopus, Zebra fish, and *Drosophila*, among others, have provided new insight into the regulation of the cell cycle, organelle biosynthesis and trafficking, cell fate and lineage decisions during development, as well as providing the fundamental principles for transcriptional/translational/post-translational regulation. Indeed, the conservation of structure-function principles exhibited by such systems has generated new insight into these and other regulatory systems utilized by mammalian cells. Moreover, a resolution of the genetic structure of the mammalian homologs for such genes in non-mammalian species has often led to a discernment of their function in mammals, even though the delineation of the function of a particular, homologous mammalian gene or gene fragment may well be serendipitous. In many cases, it is the result produced by expression and differential cDNA cloning strategies that manifest mammalian DNA sequences with homology to genes previously identified in more primitive species.

During the past decade, differential cDNA cloning methods, including e.g., conventional subtractive hybridization (Hla and Maciag, *Biochem. Biophys. Res. Commun.* 167:637–643 (1990a)), differential polymerase chain reaction (PCR)-oriented hybridization (Hla and Maciag, *J. Biol. Chem.* 265:9308–9313 (1990b)), and more recently, a modification of the differential display (Zimrin et al., *Biochem. Biophys. Res. Commun.* 213:630–638 (1995)) were used to identify genes induced during the process of human umbilical vein endothelial cell (HUVEC) differentiation in vitro. Very early studies disclosed that HUVEC populations are able to generate capillary-like, lumen-containing structures when introduced into a growth-limited environment in vitro (Maciag et al., *J. Cell Biol.* 94:511–520 (1982)). These studies permitted the identification and characterization of protein components of the extracellular matrix as inducers of this differentiation process, while at the same time defining the capillary-like structures as non-terminally differentiated (Maciag, 1984). Additional experiments have elucidated the importance of polypeptide cytokines, such as IL1 (Maier et al., *J. Biol. Chem.* 265:10805–10808 (1990a)), and IFNγ (Friesel et al., *J. Cell Biol.* 104:689–696 (1987)) as inducers of HUVEC differentiation in vitro, and ultimately lead to an understanding that the precursor form of IL-1α was responsible for the induction of HUVEC senescence in vitro (Maciag et al., *J. Cell Biol.* 91:420–426 (1981); Maier et al., *Science* 249:1570–1574 (1990b))—the only truly terminal HUVEC phenotype identified to date. Summarized in FIG. 1.

Recent research has employed differential cDNA cloning methods, which permits the identification of new and very interesting genes. However, until very recently, establishing their identity did not provide insight into the mechanism of HUVEC differentiation. Current research has focused upon the fibroblast growth factor (FGF) and interleukin (IL)-1 gene families as regulators of the angiogenesis process, both in vitro and in vivo (Friesel et al., FASEB J9:919–925 (1995); Zimrin et al., *J. Clin. Invest.* 97:1359 (1996)). The human umbilical vein endothelial cell (HUVEC) has proven to be an effective model for studying the signal pathways utilized by FGF-1 to initiate HUVEC migration and growth, the role of IL-1α as an intracellular inhibitor of FGF-1 function and modifier of HUVEC senescence, and the interplay between the FGF and the IL-1 gene families as key effectors of HUVEC differentiation in vitro. Such insight has enabled the present inventors to use modern molecular methods to identify a key regulatory ligand-receptor signaling system, which is able to both induce capillary endothelial cell migration and repress large vessel endothelial cell migration.

The Jagged/Serrate/Delta-Notch/Lin/Glp signaling system, originally described during the development of *C.*

*elegans* and *Drosophila* as an essential system instrumental in cell fate decisions, has been found to be highly conserved in mammalian cells (Nye and Kopan, *Curr. Biol.* 5:966–969 (1995)). Notch proteins comprise a family of closely-related transmembrane receptors initially identified in embryologic studies in Drosophila (Fortini and Artavanis-Tsakonas, *Cell* 75:1245–1247 (1993)). The genes encoding the Notch receptor show a high degree of structural conservation, and contain multiple EGF repeats in their extracellular domains (Coffinan et al., *Science* 249:1438–1441 (1990); Ellisen et al., *Cell* 66:649–661 (1991); Weinmaster et al., *Development* 113:199–205 (1991); Weinmaster et al., *Development* 116:931–941 (1992); Franco del Amo et al., *Development* 115:73 7–744 (1992); Reaume et al., *Dev. Biol.* 154:377–387 (1992); Lardelli and Lendahi, *Mech. Dev.* 46:123–136 (1993); Bierkamp and Campos-Ortega, *Mech. Dev.* 43:87–100 (1993); Lardelli et al., *Exp. Cell Res.* 204:364–372 (1994)). In addition to the 36 EGF repeats within the extracellular domain of Notch 1, there is a cys-rich domain composed of three Notch Lin Glp (NLG) repeats, which is important for ligand function, followed by a cys-poor region between the transmembrane and NLG domain.

The intracellular domain of Notch 1 contains six ankyrin/Cdc10 repeats positioned between two nuclear localization sequences (NLS) (Artavanis-Tsakonas et al., *Science* 268:225–232 (1995)). This motif is found in many functionally diverse proteins (see e.g., Bork, *Proteins* 17:363–374 (1993)), including members of the rel/NF-kB family (Blank et al., TIBS 17:135–140 (1992)), and is thought to be responsible for protein-protein interactions. Notch has been shown to interact with a novel ubiquitously distributed cytoplasmic protein deltex through its ankyrin repeats, a domain shown by deletion analysis to be necessary for activity (Matsuno et al., *Development* 121:2633–2644 (1995)).

Carboxy terminal to this region is a polyglutamine-rich domain (OPA) and a pro-glu-ser-thr (PEST) domain which may be involved in signaling protein degradation. There are numerous Notch homologs, including three Notch genes. (The corresponding structures for Lin-12 and Glp-1 are shown in FIG. 2.)

Several Notch ligands have been identified in vertebrates, including Delta, Serrate and Jagged. The Notch ligands are also transmembrane proteins, having highly conserved structures. These ligands are known to signal cell fate and pattern formation decisions through the binding to the Lin-12/Notch family of transmembrane receptors Nuskavitch and Hoffmann, *Curr. Top. Dev. Biol.* 24:289–328 (1990); Artavanis-Tsakonas and Simpson, *Trends Genet.* 7:403408 (1991); Greenwald and Rubin, *Cell* 68:271–281 (1992); Gurdon, *Cell* 68:185–199 (1992); Fortini and Artavanis-Tsakonas, 1993; and Weintraub, *Cell* 75:1241–1244 (1993)). A related protein, the Suppressor of hairless (Su(H)), when co-expressed with Notch in *Drosophila* cells, is sequestered in the cytosol, but is translocated to the nucleus when Notch binds to its ligand Delta (Fortini and Artavanis-Tsakonas, 1993). Studies with constitutively activated Notch proteins missing their extracellular domains have shown that activated Notch suppresses neurogenic and mesodermal differentiation (Coffman et al., *Cell* 73:659–671 (1993); Nye et al., *Development* 120:2421–2430 (1994)).

The Notch signaling pathway (FIG. 3), which is apparently activated by Jagged in the endothelial cell, involves cleavage of the intracellular domain by a protease, followed by nuclear trafficking of the Notch fragment and the interaction of this fragment with the $KBF_2/RBP-J_k$ transcription factor (Jarriault et al., *Nature* 377:355–358 (1995); Kopan et al., *Proc. Natl. Acad Sci.* USA 93:1683–1688 (1996)), a homolog of the *Drosophila* Suppressor of hairless gene (Schweisguth et al., *Cell* 69:1199–1212 (1992)), a basic helix-loop-helix transcription factor involved in Notch signaling in insects (Jennings et al., *Development* 120:3537–3548 (1994)) and in the mouse (Sasai et al., *Genes Dev.* 6:2620–2634 (1992)). This effector is able to repress the transcriptional activity of other genes encoding transcription factors responsible for entry into the terminal differentiation program (Nye et al., 1994; Kopan et al., *J. Cell. Physiol.* 125:1–9 (1994)).

The Jagged gene encodes a transmembrane protein which is directed to the cell surface by the presence of a signal peptide sequence (Lindsell et al., *Cell* 80:909–917 (1995)). While the intracellular domain contains a sequence with no known homology to intracellular regions of other transmembrane structures, the extracellular region of the ligand contains a cys-rich region, 16 epidermal growth factor (EGF) repeats, and a DSL (Delta Serrate Lag) domain. As shown in FIG. 4, the DSL domain as well as the EGF repeats, are found in other genes including the *Drosophila* ligands, Serrate (Baker et al., *Science* 250:1370–13771990; Thomas et al., *Development* 111:749–761 (1991)) and Delta (Kopczynski et al., *Genes Dev.* 2:1723–1735 (1988)), and *C. elegans* genes Apx-1 (Henderson et al., *Development* 120:2913–2924 (1994); Mello et al., *Cell* 77:95–106 (1994)) and Lag-2 (Tax et al., *Nature* 368, 150–154 (1994)).

Nevertheless, until the discovery of the presently disclosed invention, human Jagged remained undefined and the function and relationship, if any, of the human ligand to Notch remained unknown in the art. However, there was a recognized need in the art for a complete understanding of the protein's role in the regulation of cell differentiation and regulation. As disclosed in the present invention, the human Jagged gene has now been cloned, isolated and defined, and the Jagged-Notch role in endothelial cell differentiation and/or migration has been elucidated. In addition, it is presently disclosed that the novel signaling pathway produces disparate effects on the migration of large and small vessel endothelial cells, providing what appears to be the first demonstration of a signaling difference between large and small vessel endothelial cells both in degree and direction. This highlights the potential function of a previously unknown ligand-receptor signaling pathway in the endothelial cell which is modulated during the migratory phase of angiogenesis. Moreover, the present invention provides an explanation of the previously unresolved phenomenon in which endothelial cells have been shown to reproducibly differentiate into a non-terminal and completely reversible tubular-like cell phenotype in vitro (Maciag et al., 1982). Thus, the present invention significantly advances the art, providing not only methods of regulating cell differentiation and angiogenesis, but also teaching a method for preventing the undesirable migration of specific cell types into large blood vessels following angioplastic surgery to control restenosis.

SUMMARY OF THE INVENTION

The present invention relates to a novel discovery of human Jagged and of the role of Jagged-Notch in endothelial cell migration and/or differentiation, and to the determination that the signaling pathway produces disparate effects on the migration of large and small vessel endothelial cells.

The invention provides a substantially purified Jagged protein, ie., a peptide free of the proteins with which it is normally associated, particularly a human Jagged protein; it also provides a functionally equivalent derivative, or allelic or species variant thereof. It further provides a peptide which has an amino acid sequence corresponding to SEQ ID NO:1. Moreover, the invention provides a protein which is characterized by the ability to bind to Notch.

The invention provides a substantially purified nucleic acid molecule encoding a Jagged protein, particularly a human Jagged protein; it also provides a nucleic acid molecule or DNA segment thereof encoding a functionally equivalent derivative, or allelic or species variant thereof. It further provides a nucleic acid sequence having a sequence corresponding to SEQ ID NO:2. Moreover, the invention provides a nucleic acid sequence encoding a human protein which is characterized by the ability to bind to Notch.

In addition, the invention provides a recombinant molecule comprising a vector and the nucleic acid sequence or segment thereof encoding the Jagged protein or functional portion thereof, particularly the human Jagged protein. It also provide a host cell comprising the recombinant molecule comprising a vector and the nucleic acid sequence or segment thereof encoding the Jagged protein or functional portion thereof The invention further provides the expression product of the recombinant molecule comprising a vector and the nucleic acid sequence encoding the Jagged protein.

Further, the invention provides a substantially purified, single-stranded, nucleic acid molecule comprising the antisense strand of the Jagged cDNA (γ-Jagged), particularly of the cDNA for the human Jagged protein; it also provides DNA segments which if read in the sense direction would encode a functionally equivalent derivative, or allelic or species variant thereof. It also provides the nucleic acid molecule comprising the antisense nucleotide sequence corresponding to the antisense strand of SEQ ID NO:2. Moreover, the invention provides an antisense molecule which is characterized by the ability to bind to Jagged, or a functionally equivalent derivative, or allelic or species variant thereof.

The invention also provides the polypeptide encoded by the nucleic acid molecule comprising the antisense strand of the Jagged cDNA (γ-Jagged), particularly of the cDNA for the human Jagged protein. It further provides the polypeptide encoded by the antisense Jagged molecule, wherein the polypeptide has a binding affinity to, and inhibits the activity of Jagged.

In addition, the invention provides an antibody having a binding affinity to Jagged, or a unique portion thereof.

It also provides a secondary antibody having a binding affinity to anti-Jagged, or a unique portion thereof.

The invention provides a method of decreasing the migration of endothelial cells to a site on a micro-diameter blood vessel, comprising delivering a Jagged protein, or a functionally equivalent derivative, or allelic or species variant thereof, or a secondary anti-Jagged antibody to a site from which the endothelial cells have been removed, damaged or substantially reduced. It also provides a method of decreasing the migration of endothelial cells, particularly human endothelial cells, to a site on a macro-diameter blood vessel, comprising delivering an antisense Jagged molecule (γ-Jagged) or a Jagged antibody to a site from which the endothelial cells have been removed, damaged or substantially reduced.

The invention provides a method of increasing the migration of endothelial cells, particularly human endothelial cells, to a site on a macro-diameter blood vessel, comprising delivering a Jagged protein, or a functionally equivalent derivative, or allelic or species variant thereof or a secondary anti-Jagged antibody to a site from which the endothelial cells have been removed, damaged or substantially reduced. It also provides a method of increasing the migration of endothelial cells, particularly human endothelial cells, to a site on a micro-diameter blood vessel, comprising delivering an antisense Jagged molecule (γ-Jagged) or a Jagged antibody to a site from which the endothelial cells have been removed, damaged or substantially reduced.

Moreover, the invention provides a method of decreasing the migration of smooth muscle cells, particularly human smooth muscle cells, to a site on a macro-diameter blood vessel, comprising delivering an antisense Jagged molecule (γ-Jagged) or a Jagged antibody to a site from which the endothelial cells have been removed, damaged or substantially reduced.

The invention also provides a pharmaceutical composition comprising a therapeutically effective amount of a Jagged protein, or functionally equivalent derivative, or allelic or species variant thereof particularly a human Jagged protein; and a pharmaceutically acceptable carrier. Also provided is a pharmaceutical composition comprising a therapeutically effective amount of a Jagged nucleic acid, or functionally equivalent derivative, or allelic or species variant thereof, particularly a human Jagged nucleic acid; and a pharmaceutically acceptable carrier.

In addition, the invention provides a pharmaceutical composition comprising a therapeutically effective amount of a Jagged antibody, or functionally equivalent derivative, or allelic or species variant thereof; and a pharmaceutically acceptable carrier. Also provided is a pharmaceutical composition comprising a therapeutically effective amount of a Jagged antisense molecule, or functionally equivalent derivative, or allelic or species variant thereof; and a pharmaceutically acceptable carrier. Further provided is a pharmaceutical composition comprising a therapeutically effective amount of an anti-Jagged antibody, or functionally equivalent derivative, or allelic or species variant thereof; and a pharmaceutically acceptable carrier.

The invention also provides a method of preventing or treating a disease or condition in a subject comprising administering to a subject in need of such prevention or treatment a therapeutically effective amount of a molecule which antagonizes, inhibits or prevents the function of the Notch protein; or comprising administering a therapeutically effective amount of a molecule which agonizes, enhances or stimulates the function of the Notch protein. It further provides a method of preventing or treating a disease or condition in a subject comprising administering to a subject in need of such prevention or treatment a therapeutically effective amount of a molecule which antagonizes, inhibits or prevents the function of the Jagged protein; or comprising administering a therapeutically effective amount of a molecule which agonizes, enhances or stimulates the function of the Jagged protein.

In addition, the invention provides a method of inhibiting or preventing angiogenesis in a subject comprising administering to a subject in need of such inhibition or prevention a therapeutically effective amount of Jagged or a Jagged agonist. The angiogenesis being inhibited or prevented comprises solid tumor angiogenesis, rheumatoid arthritic angiogenesis, inflammatory angiogenesis, and the like. The invention also provides a method of inhibiting or preventing restenosis of the lumen of a blood vessel, by repressing angiogenesis from the vaso vasorum, and by promoting large vessel endothelial cell migration to repair the lumen of a large blood vessel. These methods of inhibiting or preventing angiogenesis are provided in vivo and/or in vitro. Also provided are Jagged agonists comprising agents which promote the expression of Jagged, including fibrin and functional derivatives thereof and pharmacologically acceptable chemicals, and γ-idiotypic Jagged antibodies.

Moreover, the invention provides a method of promoting or enhancing angiogenesis in a subject comprising administering to a subject in need of such promotion or enhancement a therapeutically effective amount of anti-Jagged or a Jagged antagonist. The angiogenesis being promoted or enhanced comprises wound or injury repair angiogenesis, such as that which occurs in a wound or injury caused by surgery, trauma and/or disease or condition, including diabetes-related wounds or injuries. These methods of promoting or enhancing angiogenesis are provided in vivo and/or in vitro. Also provided are Jagged antagonists comprising Jagged antibodies, anti-sense Jagged, Jagged mutants and pharmacologically acceptable chemicals.

The invention further provides a method for affecting cell differentiation of cells comprising the mesoderm, endoderm, ectoderm and/or neuroderm. Also provided is a method for affecting cell differentiation of cells, wherein the cell types affected comprise hematopoietic stem cells, epithelial cells, vascular smooth muscle cells and dendritic cells.

In addition, the invention provides a pharmaceutical composition used in any of the previously disclosed methods.

Additional objects, advantages and novel features of the invention will be set forth in part in the description which follows, and in part will become apparent to those skilled in the art on examination of the following, or may be learned by practice of the invention.

BRIEF DESCRIPTION OF THE FIGURES

Figure 8C:
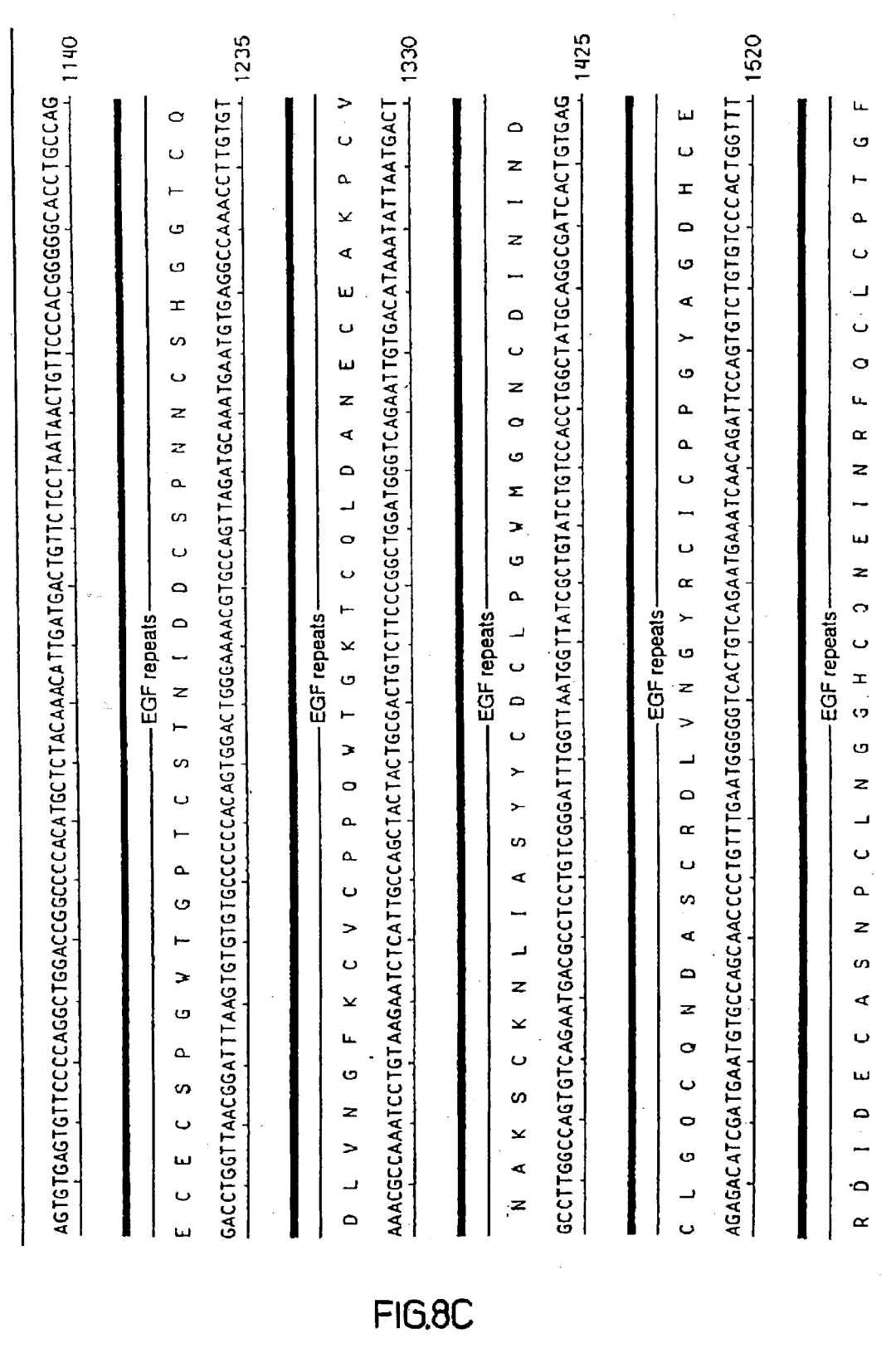

FIGS. 8A to 8J. Amino acid (SEQ ID NO:1) and nucleic acid (SEQ ID NO:2) sequences of human Jagged.

DESCRIPTION OF PREFERRED EMBODIMENTS OF THE INVENTION

Definitions

Figure 1:
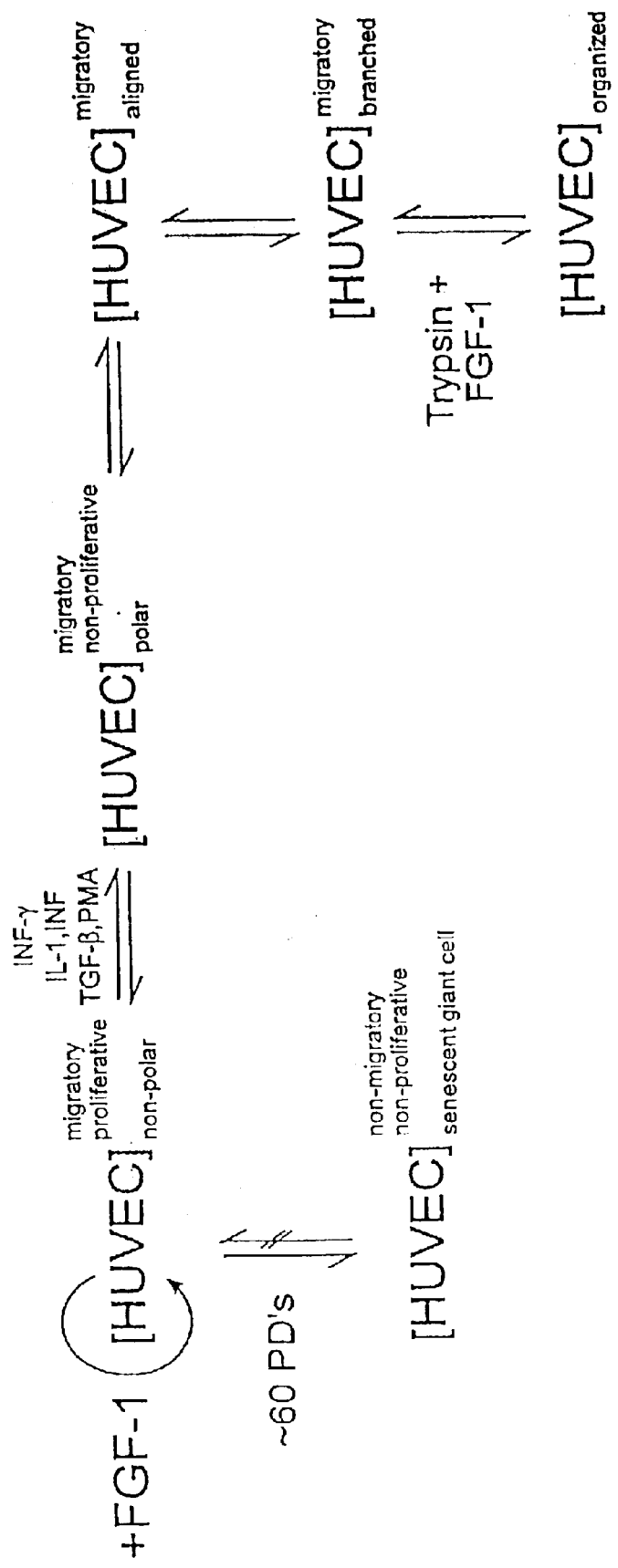
FIG. 1. Illustration of the phenotypic alterations of HUVEC by cytokines. Early studies demonstrated that HUVEC populations are able to generate capillary-like, lumen-containing structures when introduced into a growth-limited environment in vitro. However, exposure of an HUVEC population to polypeptide cytokines, such as IL-1 and IFNγ, as inducers of HUVEC differentiation in vitro, lead to an understanding that the precursor form of IL-1α was responsible for the induction of HUVEC senescence in vitro, the only truly terminal HUVEC phenotype identified to date. (PD=population doubling).

In the description that follows, a number of terms used in the claims as well as in recombinant DNA technology are extensively utilized. In order to provide a clear and consistent understanding of the specification and claims, including the scope to be given such claims, the following definitions are provided.

DNA segment. A DNA segment, as is generally understood and as used herein, refers to a molecule comprising a linear stretch of nucleotides wherein the nucleotides are present in a sequence that encodes, through the genetic code, a molecule comprising a linear sequence of amino acid residues that is referred to as a protein, a protein fragment, or a polypeptide.

Gene. A DNA sequence related to a single polypeptide chain or protein, and as used herein includes the 5' and 3' ends. The polypeptide can be encoded by a full-length sequence or any portion of the coding sequence, so long as the functional activity of the protein is retained.

A "complimentary DNA" or "cDNA" gene includes recombinant genes synthesized by reverse transcription of messenger RNA ("mRNA") lacking intervening sequences (introns).

Structural gene. A DNA sequence that is transcribed into mRNA that is then translated into a sequence of amino acids characteristic of a specific polypeptide. Typically the first nucleotide of the first translated codon is numbered +1, and the nucleotides are numbered consecutively with positive integers through the translated region of the structural gene and into the 3' untranslated region. The numbering of the nucleotides in the promoter and regulatory region 5' to the translated region proceeds consecutively with negative integers with the 5' nucleotide next to the first translated nucleotide being numbered −1.

Gel electrophoresis. To detect determine the size of particular DNA fragments, the most common technique (although not the only one) is agarose gel electrophoresis, which is based on the principle that DNA molecules migrate through the gel as though it were a sieve that retards the movement of the largest molecules to the greatest extend, and the movement of the smallest molecules to the least extent. The fractionated molecules can be visualized by staining, permitting the DNA fragments of a genome to be visualized. However, most genomes, including the human genome, contain too many DNA sequences to produce an easily visualized pattern. Thus, a methodology referred as "Southern hybridization" (or "blotting") is used to visualize small subsets of fragments. By this procedure the fractionated DNA is physically transferred onto nitrocellulose filter paper or another appropriate surface using recognized methods. Note that RNA fragments can be similarly visualized by the "northern blot" process.

Nucleic acid hybridization. This process depends on the principle that two single-stranded molecules that have complimentary base sequences will reform into the thermodynamically favored double-stranded configuration ("reanneal") if they are mixed in solution under the proper conditions. The reannealling process will occur even if one of the single strands is immobilized.

Hybridization probe. To visualize a particular DNA sequence in the hybridization procedure, a labeled DNA molecule or hybridization probe is reacted to the fractionated nucleic acid bound to the nitrocellulose filter. The areas on the filter that carry nucleic acid sequences complementary to the labeled DNA probe become labeled themselves as a consequence of the reannealing reaction. The areas of the filter that exhibit such labeling are visualized. The hybridization probe is generally produced by molecular cloning of a specific DNA sequence.

Oligonucleotide or Oligomer. A molecule comprised of two or more deoxyribonucleotides or ribonucleotides, preferably more than three. Its exact size will depend on many factors, which in turn depend on the ultimate function or use of the oligonucleotide. An oligonucleotide may be derived synthetically or by cloning.

Sequence Amplification. A method for generating large amounts of a target sequence. In general, one or more amplification primers are annealed to a nucleic acid sequence. Using appropriate enzymes, sequences found adjacent to, or in between the primers are amplified.

Amplification primer. An oligonucleotide which is capable of annealing adjacent to a target sequence and serving as an initiation point for DNA synthesis when placed under conditions in which synthesis of a primer extension product which is complementary to a nucleic acid strand is initiated.

Vector. A plasmid or phage DNA or other DNA sequence into which DNA may be inserted to be cloned. The vector may replicate autonomously in a host cell, and may be further characterized by one or a small number of endonuclease recognition sites at which such DNA sequences may be cut in a determinable fashion and into which DNA may be inserted. The vector may further contain a marker suitable for use in the identification of cells transformed with the vector. The words "cloning vehicle" are sometimes used for "vector."

Expression. Expression is the process by which a structural gene produces a polypeptide. It involves transcription of the gene into mRNA, and the translation of such mRNA into polypeptide(s).

Expression vector. A vector or vehicle similar to a cloning vector but which is capable of expressing a gene which has been cloned into it, after transformation into a host. The cloned gene is usually placed under the control of (i.e., operably linked to) certain control sequences such as promoter sequences. Expression control sequences will vary depending on whether the vector is designed to express the operably linked gene in a prokaryotic or eukaryotic host and may additionally contain transcriptional elements such as enhancer elements, termination sequences, tissue-specificity elements, and/or translational initiation and termination sites.

Functional derivative. A "functional derivative" of a sequence, either protein or nucleic acid, is a molecule that possesses a biological activity (either functional or structural) that is substantially similar to a biological activity of the protein or nucleic acid sequence. A functional derivative of a protein may or may not contain post-translational modifications such as covalently linked carbohydrate, depending on the necessity of such modifications for the performance of a specific function. The term "functional derivative" is intended to include the "fragments," "segments," "variants," "analogs," or "chemical derivatives" of a molecule.

As used herein, a molecule is said to be a "chemical derivative" of another molecule when it contains additional chemical moieties not normally a part of the molecule. Such moieties may improve the molecule's solubility, absorption, biological half life, and the like. The moieties may alternatively decrease the toxicity of the molecule, eliminate or attenuate any undesirable side effect of the molecule, and the like. Moieties capable of mediating such effects are disclosed in *Remington's Pharmaceutical Sciences* (1980). Procedures for coupling such moieties to a molecule are well known in the art.

Variant. A "variant" or "allelic or species variant" of a protein or nucleic acid is meant to refer to a molecule substantially similar in structure and biological activity to either the protein or nucleic acid. Thus, provided that two molecules possess a common activity and may substitute for each other, they are considered variants as that term is used herein even if the composition or secondary, tertiary, or quaternary structure of one of the molecules is not identical to that found in the other, or if the amino acid or nucleotide sequence is not identical.

Substantially pure. A "substantially pure" protein or nucleic acid is a protein or nucleic acid preparation that is generally lacking in other cellular components with which it is normally associated in vivo.

Ligand. "Ligand" refers to any protein or proteins that may interact with a receptor binding domain, thus having a "binding affinity" for such domain. Ligands may be soluble or membrane bound, and they may be a naturally occurring protein, or synthetically or recombinantly produced. The ligand may also be a nonprotein molecule that acts as ligand when it interacts with the receptor binding domain. Interactions between the ligand and receptor binding domain include, but are not limited to, any covalent or non-covalent interactions. The receptor binding domain is any region of the receptor molecule, e.g. Notch, that interacts directly or indirectly with the ligand, e.g., Jagged. If the Notch-Jagged interaction acts as an on-off switch, Jagged may provide the receptor binding domain, and Notch or a component produced as a result of the Notch-Jagged interaction may act as the ligand.

"Antisense nucleic acid sequence," "antisense sequence," "antisense DNA molecule" or "antisense gene" refer to pseudogenes which are constructed by reversing the orientation of the gene with regard to its promoter, so that the antisense strand is transcribed. The term also refers to the antisense strand of RNA or of cDNA which compliments the strand of DNA encoding the protein or peptide of interest. In either case, when introduced into a cell under the control of a promoter, the anti-sense nucleic acid sequence inhibits the synthesis of the protein of interest from the endogenous gene. The inhibition appears to depend on the formation of an RNA-RNA or cDNA-RNA duplex in the nucleus or in the cytoplasm. Thus, if the antisense gene is stably introduced into a cultured cell, the normal processing and/or transport is affected if a sense-antisense duplex forms in the nucleus; or if antisense RNA is introduced into the cytoplasm of the cell, the expression or translation of the endogenous product is inhibited. Such antisense nucleic acid sequences may further include modifications which could affect the biological activity of the antisense molecule, or its manner or rate of expression. Such modifications may also include, e.g., mutations, insertions, deletions, or substitutions of one or more nucleotides that do not affect the function of the antisense molecule, but which may affect intracellular localization. Modifications include, but are not limited to, 5-fluorouracil, 5-bromouracil, 5-chlorouracil, 5-iodouracil, hypoxanthine, xanthine, 4-acetylcytosine, 5-(carboxyhydroxmethyl uracil, 5-carboxyhydroxmethyl-2-thiouridine, 5-carboxymethylaminomethyl uracil, dihydrouracil, beta-D-galactosylqueosine, inosine, N6-isopentyladenine, 1-methylguanine, 1-methyinosine, 2,2dimthylguanine, 2-methyladenine, 2-methylguanine, 3-methylcytosine, 5-methylcytosine, N6-adenine, 7-methylguanine, 5-methylaminomethyluracil, 5-methylaminomethyl-2-thioracil, beta-D-mannosylqueosine, 5'-methoxycarboxymethyluracil, 5-methyluracil, 2-methylthio-N6-isopentenyladenine, uracil-5oxyacetic acid, wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid, 5-methy-2-thiouracil, 3-(3-amino-3-N-2-carboxpropyl) uracil, and 2,6-diaminopurine.

The nucleic acid sequence may determine an uninterrupted antisense RNA sequence or it may include one or more introns. The antisense Jagged molecule(s) of the present invention are referred to as γ-Jagged.

Steady-state level. The term refers to a stable condition that does not change over time, or the state in which change in one direction or production of a component is continually balanced by a compensatory change in another.

Preferred Embodiments

Angiogenesis, or the formation of new blood vessels, plays a central role in a number of physiologic and pathologic conditions, including placental development, wound healing, rheumatoid arthritis, diabetic retinopathy and solid tumor growth and metastasis. Endothelial cells comprise a monolayer lining the luminal surface of all blood vessels, thereby playing a central role in this process. In vitro populations of endothelial cells isolated from both large vessels and microvessels can be induced to mimic this differentiation process by forming a capillary-like network. Three-dimensional fibrin gels have been used to mimic angiogenesis, as an in vitro corollary of the in vivo phenomenon since endothelial cells invade blood clots in the process of wound repair.

Cellular differentiation is a well documented process in vitro, generally requiring a transcriptional component for induction. However, in contrast to most cell types, endothelial cell differentiation has been shown to be reversible. Digestion of the endothelial cellular networks formed in vitro, and subsequent culture of the cells in the presence of FGF- 1 causes them to revert to an undifferentiated phenotype (see, e.g., Maciag et al., *J. Cel Biol.* 94:511–520 (1982)). However, endothelial cell differentiation has also been shown to have a transcriptional basis. Endothelial cell (HUVEC) organization into a cellular network has been shown to be associated with an increase in the transcript encoding fibronectin, and a decrease in the transcript encoding sis, which reverses when the cellular network is digested with proteases and the cells revert to the proliferative phenotype (see e.g., Jaye et al., *Science* 228:882–885 (1985)).

HUVEC are capable of two different behaviors, both of which are termed "differentiation." The first is the formation of a two dimensional network involving cell elongation, anastomosis and branching that does not require transcription and translation, but requires post-translational modification. The second is a more complex three-dimensional process resulting in a capillary network containing lumens, which Zimrin et al. (1995) have shown requires both transcriptional and post-translational events. In addition, Zimrin et al. (1995) has defined the modified differential display technique as applied to endothelial cells and demonstrated that it is a very useful method of isolating transcripts which are differentially expressed as endothelial cells differentiate.

Thus, in the present invention, using a modification of the differential display method, the human homolog of the Jagged ligand for the Notch receptor has been isolated from human umbilical vein endothelial cells (HUVEC) invading a fibrin gel. The addition of an antisense Jagged oligonucleotide to bovine microvascular endothelial cells on collagen resulted in a marked increase in their invasion into the collagen gel in response to FGF-2. However, while the antisense Jagged oligonucleotide of the present invention was also able to increase the migration of bovine microvascular endothelial cells on fibronectin, the oligonucleotide significantly decreased the migration of bovine endothelial cells derived from the aorta, suggesting a divergence in the mechanism utilized by two different endothelial cell populations to respond to the Notch signaling system.

The distinction between microvascular and large vessel endothelium is well recognized as a part of the heterogeneity of the vascular endothelium in general and this is reflected in the properties of endothelial cells from different sources in cell culture (Carson and Haudenschild, In Vitro 22:344–354 (1986)), and in organ-specific expression of different adhesion molecules, cell surface glycoproteins and lectin-binding sites (Gumkowski et al., *Blood Vessels* 24:11 (1987)).

Briefly, to identify the molecular events necessary in the process of angiogenesis, a modified differential display procedure was used to isolate messages that were differentially expressed in HUVEC plated on fibrin in the presence of FGF-1 over the course of 24 hours. As described in Example 2, one of the cDNAs that was amplified at 2 hours, and which was found to be highly homologous to the rat Jagged transcript was identified as an isolate of the human Jagged homolog. The putative protein sequence of the present invention includes a signal peptide, a DSL domain shared by the Notch ligands Delta, Serrate, LAG-2 and APX-1, 16 tandem epidermal growth factor-like repeats, a cysteine-rich region, a transmembrane domain and a 125 base pair cytoplasmic tail. The 5' end of the sequence of the human Jagged isolate corresponds to position 417 of the rat sequence, at the eleventh codon of the predicted 21 residue signal peptide.

Figure 5:
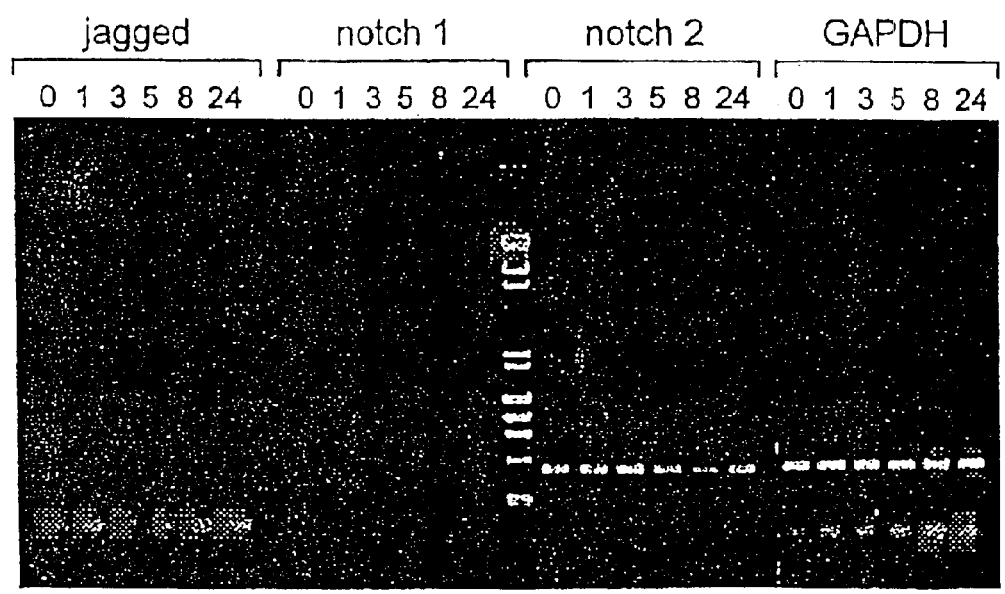
FIG. 5. RT-PCR analysis of steady-state levels of Jagged, Notch 1 and Notch 2 transcripts in HUVEC. Glyceraldehyde-3 -phosphate dehydrogenase (GAPDH) was used as a positive control.

To investigate the role of Jagged and Notch in endothelial cell behavior, reverse transcription and polymerase chain reaction amplification (RT-PCR) was used to evaluate the steady-state message levels of Jagged and two related Notch proteins, human TAN-1 and human Notch group protein, in human endothelial cells on fibrin (FIG. 5). Although the Jagged message was found to be up-regulated in populations of HUVEC exposed to fibrin at the 3 hour timepoint, the message levels of the two Notch proteins was not changed over the course of 24 hours. Thus, it is shown in the present invention that the human endothelial cell population is capable of expressing both the Jagged ligand and the Notch receptor, indicating that the human endothelial cell is completing an autocrine signal using the Notch signal transduction pathway. The data do not distinguish, however, between a homogenous population expressing both Notch and Jagged proteins, or heterogeneous subpopulations of endothelial cells that display Notch, Jagged, both or neither protein.

Therefore, to delineate a functional role for Jagged, an antisense Jagged oligonucleotide was designed in the present invention, which encompassed the Kozak consensus region, the ATG start codon and the next three codons of the rat Jagged cDNA sequence. Similar strategies have previously proved useful as a means of repressing the translational efficiency of a wide variety of transcripts in vitro (see, Scanlon et al., *FASEB J.* 9:1288–1296 (1995); Maier et al., 1990b).

Figure 6:
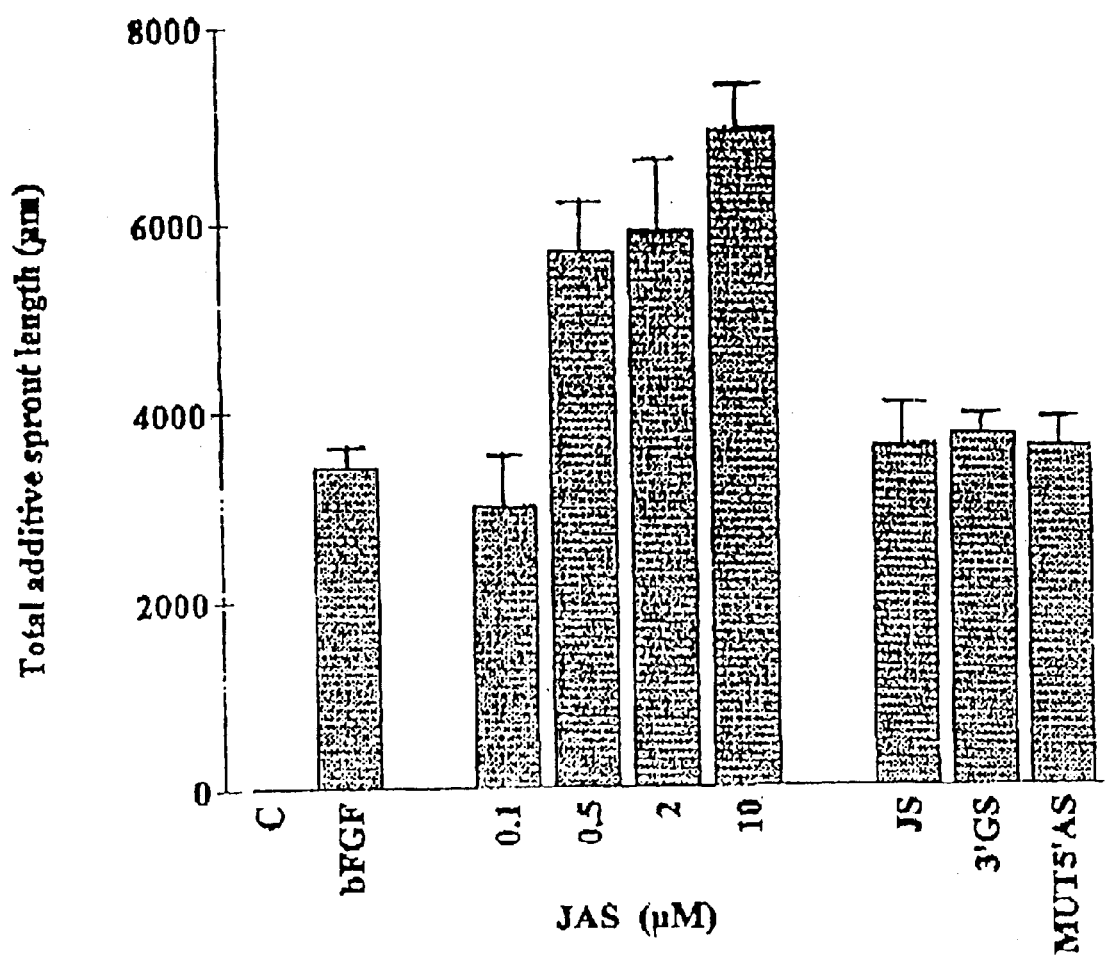
FIG. 6. Graphic representation of the effect of the antisense Jagged oligonucleotide on BMBC sprout formation, as compared with the effect on three control oligomers, a Jagged sense oligonucleotide, a 3' antisense Jagged oligomer, and a mutated 5' antisense Jagged oligomer.

Because endothelial cell migration is an important component of angiogenesis, endothelial cell behavior was evaluated under conditions of sprout formation (Montesano and Orci, *Cell* 42:469–477 (1985)) and migration (Sato and Rifkin, *J. Cell Biol.* 107:1199–1205 (1988)). The addition of the oligonucleotide to bovine microvascular endothelial cells plated on collagen at varying concentrations resulted in an oligonucleotide-induced dose-dependent increase in the total length of sprout formation observed in response to the addition of FGF-2 (FIG. 6). The addition of several control oligonucleotides, including a sense oligonucleotide covering the same sequence, a 5' antisense oligonucleotide with every third base mutated, and a random oligonucleotide, had no effect on the total length of sprout formation (FIG. 6). Thus, the addition of the antisense Jagged oligonucleotide significantly enhanced endothelial cell sprout formation beyond the level achieved by FGF-2.

These data were unusual since endothelial cell sprout formation requires cell migration as a component, and the Jagged cDNA had been isolated from a human endothelial cell system where migration into the fibrin clot also occurs. Consequently, the effect of the antisense Jagged oligonucleotide was studied on capillary and large vessel endothelial cell migration, respectively. It was found that while a bovine microvascular endothelial cell population exhibited a significant dose-dependent increase in their migration in the presence of the Jagged antisense oligonucleotide (FIG. 7A), the migration of bovine aorta endothelial cells was significantly attenuated in a dose-dependent fashion by the antisense Jagged oligonucleotide (FIG. 7B). Thus, the ability of Jagged-Notch signaling to modify endothelial cells was dependent upon the anatomic source of the endothelial cells.

Since the endothelial cells studied were from both large and small vessels responded to the antisense Jagged oligonucleotide in a disparate manner, and both cellular populations are likely to express the Notch receptor, the difference in their response to the Jagged antisense oligonucleotide indicates for the first time that there are differences between large and small vessels in the Notch signaling pathway. Although it has been documented that cells isolated from small vessels are able to undergo the phenotypic changes characteristic of capillary formation more readily than endothelial cells isolated from large vessels (Ingber and Folkman, *J. Cell Biol.* 109:317–330 (1989)), the novel response to the Jagged antisense oligonucleotide disclosed in the present invention represents the first demonstration of an effect not only different in degree but also in direction.

The present embodiments further demonstrate that the addition of exogenous Jagged (or enhanced expression of Jagged) produces an effect opposite to that seen in Examples 5–7. In other words, the addition or increased expression of Jagged will decrease the migration and invasion of microvascular cells from the vaso vasorum, and increase or stimulate the migration of large vessel endothelial cells.

The clinical importance of the disparate effect of the Jagged-Notch signaling pathway on the macro- and microdiameter blood vessels is significant, offering a solution to many aspects of vascular pathophysiology. For example, the morbidity and mortality from hypertension is clearly based on the disease of the large vessels (atherosclerosis and stroke), but in the major forms of hypertension, the actual cause for elevated blood pressure lies in the peripheral vascular beds (arterioles and microvasculature) (Chobanian et al., *Hypertension* 8:15–21 (1986)). The presently defined compositions and methods may resolve the previously unanswered question of how hypertension could be directly related to the aortic intima and atherosclerosis, and vice versa, how known atherogenic risk factors could affect the microvascular endothelium (Chan et al., *Microvasc. Res.* 18:353–369 (1979)).

Moreover, the presently embodied compositions and methods are useful for the modification of a post-angioplastic situation, when one or more large coronary vessel have been stripped of their endothelial cell lining. One of the most serious complications limiting the value of the angioplastic procedure is the occurrence of restenosis or the rapid migration and proliferation of smooth muscle cells, monocytes/macrophages, platelets, and endothelium at the wound site resulting in a reocclusion of the vessel that may be more extensive than before treatment (see numerous review articles on the subject, e.g., Schwartz et al., *Atherosclerosis* 1:107–161 (1981)). However, treating the wounded or injured area with a therapeutic amount of additional recombinant Jagged protein, or a functionally equivalent drug or protein having the ability to signal Notch, will prevent or inhibit reocclusion by increasing the migration of the large vessel endothelial cells on the borders of the lesion into the denuded area to cover the lesion, while also decreasing emergence of the micro-vascular cells (smooth muscle, endothelial, macrophage, etc) from the vaso vasorum and providing the nutrient microvessels or sprouts to supply the proliferating smooth muscle cells.

In a preferred embodiment, the present invention provides highly purified Jagged protein. As used herein, a protein is said to be highly purified if the protein possesses a specific activity that is greater than that found in whole cell extracts containing the protein.

Any eukaryotic organism can be used as a source of Jagged, or the genes encoding same, as long as the source organism naturally contains the ligand or its equivalent. As used herein, "source organism" refers to the original organism from which the amino acid or DNA sequence is derived, regardless of the organism the ligand is expressed in or ultimately isolated from. For example, a human is said to be the "source organism" of Jagged expressed by an insect expression system as long as the amino acid sequence is that of human Jagged. The most preferred source organism is human.

A variety of methodologies known in the art can be utilized to obtain the Jagged proteins of the present invention. In one embodiment, the Jagged is purified from tissues or cells which naturally produce it, such as HUVEC. One skilled in the art can readily follow known methods for isolating proteins in order to obtain the Jagged protein. These include, but are not limited to, immunochromotography, size-exclusion chromatography, ion-exchange chromatography, affinity chromatography, HPLC, and the methods set forth by example in the present disclosure. One skilled in the art can readily adapt known purification schemes to delete certain steps or to incorporate additional purification procedures.

In another embodiment, the ligand is purified from cells which have been altered to express the desired protein. As used herein, a cell is said to be "altered to express a desired protein" when the cell, through genetic manipulation, is made to produce a protein which it normally does not produce, or which the cell normally produces at low levels. One skilled in the art can readily adapt procedures for introducing and expressing either genormic or cDNA sequences into either eukaryotic or prokalyotic cells, in order to generate a cell which produces the desired protein.

There are a variety of source organisms for DNA encoding the desired protein. The more preferred source is the endothelial cell. The most preferred source is the human endothelial cell. The embodied methods are readily adapted to use of an HUVEC population as a model to be evaluated in comparison with HU artery (A) EC and human cells obtained from other anatomic sites. These include human adipose-derived microvascular endothelial cells (HMEC), human dermis-derived capillary endothelial cells (HCEC) and human saphenous vein (HSVEC) and artery (HSAEC). Many human endothelial cell populations are readily available from commercial (HMEC and HCEC) and academic sources (HSVEC and HSAEC; Dr. Michael Watkins, Dept. of Surgery, Boston University, and HUAEC; Dr. Victor van Hinsbergh, Gabius Institute, Netherlands).

In yet another embodiment, since probes are available which are capable of hybridizing to Jagged, DNA sequences encoding the desired nucleic acid sequence encoding the protein of interest can be obtained by routine hybridization and selection from any host which possesses these receptors. A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene sequence expression. The precise nature of the regulatory regions needed for gene sequence expression may vary from organism to organism, but shall in general include a promoter region which, in prokaryotes, contains both the promoter (which directs the initiation of RNA transcription) as well as the DNA sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence encoding Jagged may be obtained by the above-described methods. This region may be retained for its transcriptional termination regulatory sequences, such as termination and polyadenylation. Thus, by retaining the 3'-region naturally contiguous to the DNA sequence encoding Jagged, the transcriptional termination signals may be provided. Where the transcriptional termination signals are not satisfactorily functional in the expression host cell, then a 3' region functional in the host cell maybe substituted.

Two DNA sequences (such as a promoter region sequence and the Jagged encoding sequence) are said to be operably linked if the nature of the linkage between the two DNA sequences does not (1) result in the introduction of a frame-shift mutation (2) interfere with the ability of the promoter region sequence to direct the transcription of the Jagged gene sequence, or (3) interfere with the ability of the Jagged gene sequence to be transcribed by the promoter region sequence. Thus, a promoter region would be operably linked to a DNA sequence if the promoter were capable of effecting transcription of that DNA sequence. To express Jagged, transcriptional and translational signals recognized by an appropriate host are necessary.

In another embodiment, the nucleic acids sequences of the present invention are under controlled expression by the animal or human patient. In the alternative, the nucleic acids sequences are administered to the patient in need of gene therapy, intravenously, intramuscularly, subcutaneously, enterally, topically, parenterally or surgically. When administering the nucleic acids by injection, the administration may be by continuous administration, or by single or multiple administrations. The gene therapy is intended to be provided to the recipient mammal in a "pharmacologically or pharmaceutically acceptable form" in an amount sufficient to "therapeutically effective." The nuceic acid is said to be in "pharmaceutically or pharmacologically acceptable form" if its administration can be tolerated by a recipient patient. An amount is said to be "therapeutically effective" (also referred to here and elsewhere as "an effective amount") if the dosage, route of administration, etc., of the agent are sufficient to affect a response to Jagged. The nucleic acid is considered to be in "pharmaceutically or pharmacologically acceptable form" if its administration can be tolerated by a recipient patient.

The present invention further encompasses the expression of the Jagged protein (or a functional derivative thereof) in either prokaryotic or eukaryotic cells. Preferred prokaryotic hosts include bacteria such as *E. coli, Bacillus, Streptomyces, Pseudomonas, Salmonella, Serratia*, etc. Under such conditions, the Jagged will not be glycosylated. The prokaryotic host must be compatible with the replicon and control sequences in the expression plasmid.

However, prokaryotic systems may not prove efficacious for the expression of a soluble Jagged ligand, since the protein of interest contains 1048 residues encompassing residue 22 (after the signal sequence) to residue 1069 (prior to the transmembrane domain). While prokaryotic expression systems, e.g., pET3c, have been used to express high molecular weight proteins, such as a biologically active (molecular weight $(M_r)$~118 kDa) FGF-1:β-galactosidase chimera (Shi et al., submitted to *J. Biol. Chem.*, 1996), successful folding and disulfide bond formation for the multiple EGF repeats (three disulfide bonds per EGF repeat) in the Jagged sequence may be difficult to accomplish in bacteria.

Nevertheless, to express Jagged (or a functional derivative thereof) in a prokaryotic cell, it is necessary to operably link the Jagged coding sequence to a functional prokaryotic promoter. Such promoters may be either constitutive or, more preferably, regulatable (i.e., inducible or derepressible). Examples of constitutive promoters include the int promoter of bacteriophage λ, the bla promoter of the β-lactamase gene sequence of pBR322, and the CAT promoter of the chloramphenicol acetyl transferase gene sequence of pPR325, etc. Examples of inducible prokaryotic promoters include the major right and left promoters of bacteriophage λ ($P_L$ and $P_R$), the trp, reca, lacZ, lacI, and gal promoters of *E. coli*, the α-amylase (Ulmanen, I., et al., *J. Bacteriol.* 162:176–182 (1985)) and the ζ-28-specific promoters of *B. subtilis* (Gilman, M. Z., et al., *Gene sequence* 32:11–20 (1984)), the promoters of the bacteriophages of Bacilli (Gryczan, T. J., In: *The Molecular Biology of the Bacilli*, Academic Press, Inc., N.Y. (1982)), and Streptomyces promoters (Ward, J. M., et al., *Mol. Gen. Genet.* 203:468–478 (1986)). See also reviews by Glick B. R., (*J. Ind Microbiol.* 1:277–282 (1987)); Cenatiempo, Y. (*Biochimie* 68:505–516 (1986)); and Gottesman, S. (*Ann. Rev. Genet.* 18:415–442 (1984)).

Proper expression in a prokaryotic cell also requires the presence of a ribosome binding site upstream of the gene sequence-encoding sequence. Such ribosome binding sites are disclosed, for example, by Gold, L., et al. (*Ann. Rev. Microbiol.* 35:365–404 (1981)).

Preferred eukaryotic hosts include yeast, fungi, insect cells, mammalian cells, either in vivo or in tissue culture. Mammalian cells which may be useful as hosts include HeLa cells, cells of fibroblast origin such as VERO or CHO-K1, or cells of lymphoid origin such as the hybridoma SP2/O-AG14 or the myeloma P3×63Sg8, and their derivatives. Preferred mammalian host cells include SP2/0 and J558L, as well as neuroblastoma cell lines such as IMR 332 that may provide better capacities for correct post-translational processing.

For a mammalian host, several possible vector systems are available for the expression of Jagged. A wide variety of transcriptional and translational regulatory sequences may be employed, depending upon the nature of the host. The transcriptional and translational regulatory signals may be derived from viral sources, such as adenovirus, bovine papilloma virus, Simian virus, or the like, where the regulatory signals are associated with a particular gene sequence which has a high level of expression. Alternatively, promoters from mammalian expression products, such as actin, collagen, myosin, etc., may be employed. Transcriptional initiation regulatory signals may be selected which allow for repression or activation, so that expression of the gene sequences can be modulated. Of interest are regulatory signals which are temperature-sensitive so that by varying the temperature, expression can be repressed or initiated, or are subject to chemical (such as metabolite) regulation.

Yeast expression systems can also carry out post-translational peptide modifications. A number of recombinant DNA strategies exist which utilize strong promoter sequences and high copy number of plasmids which can be utilized for production of the desired proteins in yeast. Yeast recognizes leader sequences on cloned mammalian gene sequence products and secretes peptides bearing leader sequences (i.e., pre-peptides). Any of a series of yeast gene sequence expression systems incorporating promoter and termination elements from the actively expressed gene sequences coding for glycolytic enzymes produced in large quantities when yeast are grown in mediums rich in glucose can be utilized. Known glycolytic gene sequences can also provide very efficient transcriptional control signals. For example, the promoter and terminator signals of the phosphoglycerate kinase gene sequence can be utilized.

The more preferred host for a protein the size of Jagged is insect cells, for example the *Drosophila* larvae. Using insect cells as hosts, the *Drosophila* alcohol dehydrogenase promoter can be used (see, e.g., Rubin, G. M., *Science* 240:1453–1459 (1988)).

The baculovirus insect cell expression system is the most preferred system for expressing the soluble Jagged construct (residues 1–1069) as a carboxy-terminal triple tandem myc-epitope repeat:glutathione-S-transferase (GST) fusion protein chimera, using conventional PCR methods (Zhan et al., *J. Biol. Chem.* 269:20221–20224 (1994)). These include the use of recombinant circle PCR to synthesize the soluble Jagged-Myc-GST construct (sJMG), the preparation and expression of the recombinant virus, AcNPV-GsJ in Sf9 cells (Summers and Smith (1988) *A Manual of Methods for aculovirus Vectors and Insect Culture Procedures* (Texas Experimental Station Bulletin #1555)), the use of GST affinity chromatography (Zhan et al., 1994) and reversed phase or ion exchange HPLC to purify the recombinant protein from Sf9 cell lysates and Myc immunoblot analysis to monitor the purification and assess the purity of the sJMG protein.

The sJMG construct may not only prove to be valuable for the baculovirus expression system, but also as a construct for the expression of a secreted and soluble extracellular Jagged ligand in mammalian cells for implantation in vivo. Thus, the sJM construct—lacking the GST fusion domain—may be inserted into the pMEXneo vector and stable NIH 3T3 cell transfectants obtained following selection with G418 as described (Zhan et al., *Biochem. Biophys. Res. Commun.* 188:982–991 (1992). Moreover, baculovirus vectors can be engineered to express large amounts of Jagged in insect cells (Jasny, B. R., *Science* 238:1653 (1987); Miller, D. W., et al., in *Genetic Engineering* (1986), Setlow, J. K., et al., eds., *Plenum*, Vol. 8, pp. 277–297).

As discussed above, expression of Jagged in eukaryotic hosts requires the use of eukaryotic regulatory regions. Such regions will, in general, include a promoter region sufficient to direct the initiation of RNA synthesis. Preferred eukaryotic promoters include: the promoter of the mouse metallothionein I gene sequence (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature* (London) 290:304–310 (1981)); the yeast gal4 gene sequence promoter (Johnston, S. A., et al., *Proc. Natl. Acad. Sci.* (USA) 79:6971–6975 (1982); Silver, P. A., et al., *Proc. Natl. Acad Sci.* (USA) 81:5951–5955 (1984)).

As is widely known, translation of eukaryotic mRNA is initiated at the codon which encodes the first methionine. For this reason, it is preferable to ensure that the linkage between a eukaryotic promoter and a DNA sequence which encodes Jagged (or a functional derivative thereof) does not contain any intervening codons which are capable of encoding a methionine (i.e., AUG). The presence of such codons results either in a formation of a fusion protein (if the AUG codon is in the same reading frame as the Jagged coding sequence) or a frame-shift mutation (if the AUG codon is not in the same reading frame as the Jagged coding sequence).

The Jagged coding sequence and an operably linked promoter may be introduced into a recipient prokaryotic or eukaryotic cell either as a non-replicating DNA (or RNA) molecule, which may either be a linear molecule or, more preferably, a closed covalent circular molecule. Since such molecules are incapable of autonomous replication, the expression of the Jagged may occur through the transient expression of the introduced sequence. Alternatively, permanent expression may occur through the integration of the introduced sequence into the host chromosome.

In one embodiment, a vector is employed which is capable of integrating the desired gene sequences into the host cell chromosome. Cells which have stably integrated the introduced DNA into their chromosomes can be selected by also introducing one or more markers which allow for selection of host cells which contain the expression vector. The marker may provide for prototrophy to an auxotrophic host, biocide resistance, e.g., antibiotics, or heavy metals, such as copper, or the like. The selectable marker gene sequence can either be directly linked to the DNA gene sequences to be expressed, or introduced into the same cell by co-transfection. Additional elements may also be needed for optimal synthesis of single chain binding protein mRNA. These elements may include splice signals, as well as transcription promoters, enhancers, and termination signals. cDNA expression vectors incorporating such elements include those described by Okayama, H., *Molec. Cell. Biol.* 3:280 (1983).

In a preferred embodiment, the introduced sequence will be incorporated into a plasmid or viral vector capable of autonomous replication in the recipient host. Any of a wide variety of vectors may be employed for this purpose. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred prokaryotic vectors include plasmids, such as those capable of replication in *E. coil* (such as, for example, pBR322, ColE1, pSC101, pACYC 184, πVX. Such plasmids are, for example, disclosed by Maniatis, T., et al. (In: *Molecular Cloning, A Laboratory Manual*, Cold Spring Harbor Press, Cold Spring Harbor, N.Y. (1982)). Bacillus plasmids include pC194, pC221, pT127, etc. Such plasmids are disclosed by Gryczan, T. (In: *The Molecular Biology of the Bacilli*, Academic Press, N.Y. (1982), pp. 307–329). Suitable *Streptomyces* plasmids include pIJ101 (Kendall, K. J., et al., *J. Bacteriol.* 169:4177–4183 (1987)), and streptomyces bacteriophages such as ϕC31 (Chater, K. F., et al., In: *Sixth International Symposium on Actinomycetales Biology*, Akademiai Kaido, Budapest, Hungary (1986), pp. 45–54). Pseudomonas plasmids are reviewed by John, J. F., et al. (*Rev. Infect. Dis.* 8:693–704 (1986)), and Izaki, K. (*Jpn. J. Bacteriol.* 33:729–742 (1978)).

Preferred eukaryotic plasmids include BPV, vaccinia, SV40, 2-micron circle, etc., or their derivatives. Such plasmids are well known in the art (Botstein, D., et al., *Miami Wntr. Symp.* 19:265–274 (1982); Broach, J. R., In: *The Molecular Biology of the Yeast Saccharomyces*: Life Cycle and Inheritance, Cold Spring Harbor Laboratory, Cold Spring Harbor, N.Y., p. 445–470 (1981); Broach, J. R., *Cell* 28:203–204 (1982); Bollon, D. P., et al., *J. Clin. Hematol. Oncol.* 10:39–48 (1980); Maniatis, T., In: Cell Biology: *A Comprehensive Treatise*, Vol. 3, Gene sequence Expression, Academic Press, N.Y., pp. 563–608 (1980)).

Once the vector or DNA sequence containing the construct(s) has been prepared for expression, the DNA construct(s) may be introduced into an appropriate host cell by any of a variety of suitable means: transformation, transfection, conjugation, protoplast fusion, electroporation, calcium phosphate-precipitation, direct microinjection, etc. After the introduction of the vector, recipient cells are grown in a selective medium, which selects for the growth of vector-containing cells. Expression of the cloned gene sequence(s) results in the production of Jagged, or fragments thereof. This can take place in the transformed cells as such, or following the induction of these cells to differentiate (for example, by administration of bromodeoxyuracil to neuroblastoma cells or the like).

The Jagged proteins (or a functional derivatives thereof) of the present invention can be used in a variety of procedures and methods, such as for the generation of antibodies, for use in identifying pharmaceutical compositions, and for studying DNA/protein interaction.

The peptides of the present invention may also be administered to a mammal intravenously, intramuscularly, subcutaneously, enterally, topically or parenterally. When administering peptides by injection, the administration may be by continuous injections, or by single or multiple injections. The peptides are intended to be provided to a recipient mammal in a "pharmacologically or pharmaceutically acceptable form" in an amount sufficient to "therapeutically effective." A peptide is considered to be in "pharmaceutically or pharmacologically acceptable form" if its administration can be tolerated by a recipient patient. An amount is said to be "therapeutically effective" (an "effective amount") if the dosage, route of administration, etc., of the agent are sufficient to affect a response to Jagged. Thus, the present peptides may be used to increase or enhance the effect of the Jagged protein.

In another embodiment of the present invention, methods for inhibiting, decreasing or preventing the activity of the Jagged peptide can be achieved by providing an agent capable of binding to the ligand (or a functional derivative thereof). Such agents include, but are not limited to: anti-sense Jagged, the antibodies to Jagged (anti-Jagged), and the secondary or anti-peptide peptides of the present invention. By decreasing the activity of Jagged, the effects which the expression of the peptide has on angiogenesis or restenosis can be modified.

In one example of the present invention, methods are presented for decreasing the expression of Jagged (or a functional derivative thereof) by means of an anti-sense strand of cDNA to disrupt the translation of the Jagged message. Specifically, a cell is modified using routine procedures such that it expresses an antisense message, a message which is complementary to the pseudogene message. By constitutively or inducibly expressing the antisense RNA, the translation of the Jagged mRNA can be regulated. Such antisense technology has been successfully applied to regulate the expression of poly(ADP-ribose) polymerase (see, Ding et al., *J. Biol. Chem.* 267 (1992)).

On the other hand, methods for stimulating, increasing or enhancing the activity of the Jagged peptide can be achieved by providing an agent capable of enhancing the binding capability or capacity of the ligand (or a functional derivative thereof), or by inhibiting or preventing a signal which would diminish or stop the expression of Jagged in the system. Such agents include, but are not limited to, the anti-antisense Jagged peptides of the present invention. By enhancing the activity of Jagged, the affect which the expression of the peptide has on angiogenesis or restenosis can also be modified.

In yet another embodiment, Jagged (or a functional derivative or variant thereof) can be used to produce antibodies or hybridomas. One skilled in the art will recognize that if an antibody is desired that will bind to Jagged, such a ligand would be generated as described above and used as an immunogen. The resulting antibodies are then screened for the ability to bind Jagged. Additionally, the antibody can be screened for its inability to bind Notch.

The antibodies utilized in the above methods can be monoclonal or polyclonal antibodies, as well fragments of these antibodies and humanized forms. Humanized forms of the antibodies of the present invention may be generated using one of the procedures known in the art such as chimerization or CDR grafting.

In general, techniques for preparing monoclonal antibodies are well known in the art (Campbell, AM., "*Monoclonal Antibody Technology: Laboratory Techniques in Biochemistry and Molecular Biology*," Elsevier Science Publishers, Amsterdam, The Netherlands (1984); St. Groth et al., *J. Immunol. Methods* 35:1–21 (1980). For example, in one embodiment an antibody capable of binding Jagged is generated by immunizing an animal with a synthetic polypeptide whose sequence is obtained from a region of the Jagged protein.

Any animal (mouse, rabbit, etc.) which is known to produce antibodies can be utilized to produce antibodies with the desired specificity, although because of the large size of the Jagged molecule, the rabbit is more preferred. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection.

The polypeptide may be modified or administered in an adjuvant in order to increase the peptide antigenicity. Methods of increasing the antigenicity of a polypeptide are well known in the art. Such procedures include coupling the antigen with a heterologous protein (such as globulin or β-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. A hybridoma is an immortalized cell line which is capable of secreting a specific monoclonal antibody.

Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175:109–124 (1988)).

Hybridomas secreting the desired antibodies are cloned and the class and subclass are determined using procedures known in the art (Campbell, A. M., *Monoclonal Antibody Technology: laboratory Techniques in Biochemistry and Molecular Biology*, Elsevier Science Publishers, Amsterdam, The Netherlands (1984)).

For polyclonal antibodies, antibody containing antisera is isolated from the immunized animal and is screened for the presence of antibodies with the desired specificity using one of the above-described procedures.

Conditions for incubating an antibody with a test sample vary. Incubating conditions depend on the format employed in the assay, the detection methods employed the nature of the test sample, and the type and nature of the antibody used in the assay. One skilled in the art will recognize that any one of the commonly available immunological assay formats (such as, radioimmunoassays, enzyme-linked immunosorbent assays, diffusion based Ouchterlony, or rocket immunofluorescent assays, or the like) can readily be adapted to employ the antibodies of the present invention. Examples of such assays can be found in Chard, T. "*An Introduction to Radioimmunoassay and Related Techniques*" Elsevier Science Publishers, Amsterdam, The Netherlands (1986); Bullock, G. R. et al., "*Techniques in Immunocytochemistry,*" Academic Press, Orlando, Fla. Vol. 1 (1982), Vol. 2 (1983), Vol. 3 (1985); Tijssen, P., "*Practice and Theory of Enzyme Immunoassays: Laboratory Techniques in Biochemistry and Molecular Biology,*" Elsevier Science Publishers, Amsterdam, The Netherlands (1985).

The anti-Jagged antibody is also effective when immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling antibodies to such solid supports are well known in the art (Weir, D. M. et al., "*Handbook of Experimental Immunology*" 4th Ed., Blackwell Scientific Publications, Oxford, England, Chapter 10 (1986), Jacoby, W. D. et al., *Meth. Enzym.* 34 Academic Press, N.Y. (1974).

Additionally, one or more of the antibodies used in the above described methods can be detectably labelled prior to use. Antibodies can be detectably labelled through the use of radioisotopes, affinity labels (such as, biotin, avidin, etc.), enzymatic labels (such as, horse radish peroxidase, alkaline phosphatase, etc.) fluorescent labels (such as, FITC or rhodamine, etc.), paramagnetic atoms, etc. Procedures for accomplishing such labelling are well-known in the art, for example see Sternberger, L. A. et al., *J. Histochem. Cytochem.* 18:315 (1970), Bayer, E. A. et al., *Meth. Enzym.* 62:308 (1979), Engval, E. et al., *Immuno.* 109:129 (1972), Goding, J. W. *J. Immunol. Meth.* 13:215 (1976). The labeled antibodies of the present invention can be used for in vitro, in vivo, and in situ assays to identify cells or tissues which express a specific protein or ligand.

In an embodiment of the above methods, the antibodies are labeled, such that a signal is produced when the antibody (s) bind to the same molecule. One such system is described in U.S. Pat. No. 4,663,278.

The antibodies or antisense peptides of the present invention may be administered to a mammal intravenously, intramuscularly, subcutaneously, enterally, topically or parenterally. When administering antibodies or peptides by injection, the administration may be by continuous injections, or by single or multiple injections.

The antibodies or antisense peptides of the present invention are intended to be provided to a recipient mammal in a "pharmaceutically acceptable form" in an amount sufficient to be "therapeutically effective" or an "effective amount". As above, an amount is said to be therapeutically effective (an effective amount), if the dosage, route of administration, etc. of the agent are sufficient to affect the response to Jagged. Thus, the present antibodies may either stimulate or enhance the effect of the Jagged protein, or they may inhibit or prevent the effect of the Jagged protein. Or, secondary antibody(s) may be designed to affect the response to the Jagged antibody(s) per se, i.e., an anti-antibody to Jagged. In the alternative, either an antibody or an anti-antibody may be designed to affect only the anti-sense strand of the ligand.

One skilled in the art can readily adapt currently available procedures to generate secondary antibody peptides capable of binding to a specific peptide sequence in order to generate rationally designed antipeptide peptides, for example see Hurby et al., Application of "Synthetic Peptides: Antisense Peptides", *In Synthetic Peptides, A User's Guide*, W. H. Freeman, N.Y., pp.289–307(1992), and Kaspczak et al., *Biochemistry* 28:9230–8 (1989). As used herein, an agent is said to be "rationally selected or designed" when the agent is chosen based on the configuration of the Jagged peptide.

Anti-peptide peptides can be generated in one of two fashions. First, the anti-peptide peptides can be generated by replacing the basic amino acid residues found in the pseudogene peptide sequence with acidic residues, while maintaining hydrophobic and uncharged polar groups. For example, lysine, arginine, and/or histidine residues are replaced with aspartic acid or glutamic acid and glutamic acid residues are replaced by lysine, arginine or histidine. Alternatively, the anti-peptide peptides of the present invention can be generated by synthesizing and expressing a peptide encoded by the antisense strand of the DNA which encodes the pseudogene peptide. Peptides produced in this fashion are, in general, similar to those described above since codons complementary to those coding for basic residues generally code for acidic residues.

To detect secondary antibodies, or in the alternative, the labelled primary antibody, labeling reagents may include, e.g., chromophobic, enzymatic, or antibody binding reagents which are capable of reacting with the labeled antibody. One skilled in the art will readily recognize that the disclosed antibodies of the present invention can readily be incorporated into one of the established kit formats which are well known in the art.

An antibody is said to be in "pharmaceutically or pharmacologically acceptable form" if its administration can be tolerated by a recipient patient. The antibodies of the present invention can be formulated according to known methods of preparing pharmaceutically useful compositions, whereby these materials, or their functional derivatives, are combined with a pharmaceutically acceptable carrier vehicle. Suitable vehicles and their formulation, inclusive of other human proteins, e.g., human serum albumin are described, for example, in Remington's Pharmaceutical Sciences, 1980).

In order to form a pharmaceutically acceptable composition which is suitable for effective administration, such compositions will contain an effective amount of an antibody of the present invention together with a suitable amount of carrier. Such carriers include, but are not limited to saline, buffered saline, dextrose, water, glycerol, ethanol, and a combination thereof. The carrier composition may be sterile. The formulation should suit the mode of administration. In addition to carriers, the antibodies of the present invention may be supplied in humanized form.

Humanized antibodies may be produced, for example by replacing an immunogenic portion of an antibody with a corresponding, but non-immunogenic portion (i.e., chimeric antibodies) (Robinson et al., International Patent Publication PCT/ US86/02269, Akira et al., European Patent Application 184,187; Taniguchi, M., European Patent Application 171, 496; Morrison et al., European Patent Application 173,494; Neuberger, M. S. et al., PCT Application WO 86/01533; Cabilly et al., European Patent Application 125,023; Better et al., *Science* 240:1041–1043 (1988); .Liu et al., *Proc. Natl. Acad Sci.* USA 84:3439–3443 (1987); Liu et al., *J. Immunol.* 139:3521–3526 (1987); Sun et al., *Proc. Natl. Acad Sci.* USA 84:214–218 (1987); Nishimura et al., *Canc. Res.* 47:999–1005 (1987); Wood et al., *Nature* 314:446–449 (1985)); Shaw et al., *J. Natl. Cancer Inst.* 80:1553–1559 (1988).

The compositions of the present invention can also include minor amounts of wetting or emulsifying agents, or pH buffering agents. The composition can be a liquid solution, suspension, emulsion, tablet, pill, capsule, sustained release formulation or powder. The composition can be formulated as a suppository with traditional binders and carriers such as triglycerides. Oral formulations can include standard carriers such as pharmaceutically acceptable mannitol, lactose, starch, magnesium stearate, sodium saccharine, cellulose, magnesium carbonate, etc.

In a preferred embodiment of the present invention, the compositions are formulated in accordance with routine procedures for intravenous administration to a subject. Typically, such compositions are carried in a sterile isotonic aqueous buffer. As needed, a composition may include a solubilizing agent and a local anesthetic. Generally, the components are supplied separately or as a mixture in unit dosage form, such as a dry lyophilized powder in a sealed container with an indication of active agent. Where the composition is administered by infusion, it may be provided with an infusion container with a sterile pharmaceutically acceptable carrier. When the composition is administered by injection, an ampoule of sterile water or buffer may be included to be mixed prior to injection.

The therapeutic compositions may also be formulated in salt form. Pharmaceutically acceptable salts include those formed with free amino groups, such as those derived from hydrochloric, phosphoric, acetic, oxalic and tartaric acids, or formed with free carboxyl groups such as those derived from sodium, potassium, ammonium, calcium, ferric hydroxides. isopropylamine, triethylamine, 2-ethylamino ethanol, histidine, procaine, etc.

The dosage of the administered agent will vary depending upon such factors as the patient's age, weight, height, sex, general medical condition, previous medical history, etc. In general, it is desirable to provide the recipient with a dosage of the antibody which is in the range of from about 1 pg/kg to 10 mg/kg (body weight of patient), although a lower or higher dosage may be administered. Suitable ranges for intravenous administration is typically about 20–500 μg of active compound per kilogram body weight. Effective doses may be extrapolated from dose-response curves derived from in vitro and in vivo animal model test systems.

Since highly purified proteins are now available, X-ray crystallography and NMR-imaging techniques can be used to identify the structure of the ligand binding site. Utilizing such information, computer modeling systems are now available that allows one to "rationally design" an agent capable of binding to a defined structure (Hodgson, *Biotechnology* 8:1245–1247 (1990)), Hodgson, *Biotechnology* 9:609–613 (1991)). As used herein an agent is said to be "rationally designed" if it is selected based on a computer model of the ligand or Notch binding site, or in the alternative, of the ligand binding site on Jagged if activation of the Notch binding site is found to act as an on/off switch affecting the continued expression of Jagged.

In another embodiment of the present invention, methods are provided for modulating the translation of RNA encoding Jagged protein in the cell. Specifically, said method comprises introducing into a cell a DNA sequence which is capable of transcribing RNA which is complimentary to the RNA encoding the Jagged protein. By introducing such a DNA sequence into a cell, antisense RNA will be produced which will hybridize and block the translation of the Jagged protein. Antisense cloning has been described by Rosenberg et al., *Nature* 313:703–706 (1985), Preiss et al., *Nature* 313:27–32 (1985), Melton, *Proc. Natl. Acad Sci. USA* 82:144–148 (1985) and Kim et al., *Cell* 42:129–138 (1985).

Transcription of the introduced DNA will result in multiple copies of antisense RNA which will be complimentary to the Jagged. By controlling the level of transcription of antisense RNA, and the tissue specificity of expression, one skilled in the art can regulate the level of translation of Jagged protein in specific cells within a patient.

In one aspect of the above-described invention, DNA response elements (RE) can be identified which are capable of either stimulating or inhibiting the binding of Jagged. In this manner, assays may be performed to determine binding agents by using any length of DNA so long as it contains at least one RE sequence. In another embodiment, the above such assays are performed in the absence of a RE. In this fashion, agents can be identified which bind to or affect the binding capacity of Jagged independently of DNA binding. Moreover, the above assay can be modified so that it is capable of identifying agents which activate transcription of DNA sequences controlled by a RE.

In the present invention, a cell or organism is altered using routine methods such that it expresses Jagged, or a functional derivative thereof. Moreover, the cell or organism may be further altered to contain a RE operably linked to a reporter sequence, such as luciferase, beta galactosidase, or chloramphenicol acyltransferase. Agents are then incubated with the cell or organism and the expression of the reporter sequence is assayed.

In an alternative usage, nuclear and/or cytosolic extracts from the altered cell containing Jagged or a functional derivative thereof are mixed with an expression module containing an RE operably linked to a reporter sequence. The extract/expression module is incubated with an agent and the expression of the reporter sequence is assayed.

In another embodiment of the present invention, kits are provided which contain the necessary reagents to carry out the previously described methods and assays.

The present invention further provides methods of regulating gene expression in a cell. For example, a cell can be altered such that it contains a DNA sequence operably linked to an RE. Additionally, the cell can be altered to control the expression of Jagged. permitting one skilled in the art to generate a cell which expresses a given sequence in response to a particular agent.

The subjects treated in accordance with the present invention include any vertebrate organism; more preferably any mammal; most preferably a human. The only limiting factor is that the organism endogenously produces Notch and/or the toporythmic genes which modulate binding to Notch.

By providing methods of affecting angiogenesis by modulating the Notch-Jagged signal pathway, the present invention provides methods and compositions which affect a number of physiologic and pathologic conditions, including placental development, wound healing, rheumatoid arthritis, diabetic retinopathy and solid tumor growth and metastasis and motor neuron disorders. The referenced wound healing includes healing of any injury or lesion in the skin, tissue, vasculature, or nervous system of the subject, and includes cell migration and differentiation of cells comprising the mesoderm, endoderm, ectoderm and/or neuroderm. The wound or injury can be the result of surgery, trauma, and/or disease or condition. Such disease and/or conditions include ischemic lesions resulting from a lack of oxygen to the cell or tissue, e.g., cerebral or cardiac infarction or ischemia, malignant lesions, infectious lesions, e.g., abscess, degenerative lesions, lesions related to nutritional disorders, neurological lesions associated with systemic diseases, e.g., diabetic neuropathy and retinopathy, systemic lupus erythematosus, carcinoma or sarcoidosis, and lesions caused by toxins, e.g., alcohol, lead, etc. Motor neuron disorders may include, e.g., amylotrophic lateral sclerosis, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and hereditary Motorsensory Neuropathy (Charcot-Marie-Tooth disease).

All essential publications mentioned herein are hereby incorporated by reference.

In order that those skilled in the art can more fully understand this invention, the following examples are set forth. These examples are included solely for the purpose of illustration, and should not be considered as expressing limitations unless so set forth in the appended claims.

EXAMPLES

In the following examples and protocols, restriction enzymes, ligase, labels, and all commercially available reagents were utilized in accordance with the manufacturer's recommendations. The cell and molecular methods utilized in this application are established in the art and will not be described in detail. However, standard methods and techniques for cloning, isolation, purification, labeling, and the like, as well as the preparation of standard reagents were performed essentially in accordance with *Molecular Cloning: A Laboratory Manual, second edition*, edited by Sambrook, Fritsch & Maniatis, Cold Spring Harbor Laboratory, 1989, and the revised third edition thereof, or as set forth in the literature references cited and incorporated herein. Methodologic details may be readily derived from the cited publications.

Example 1

Isolation of Human Endothelial Cell cDNA Induced by Exposure to Fibrin

Endothelial cells plated on fibrin organize into three dimensional tubular structures in vitro (Olander et al., *J. Cell. Physiol.* 125:1–9 (1985)), and this organizational behavior requires transcriptional responses (Zimrin et al., 1995). Using a modification of the differential display, cDNA clones were obtained that were differentially expressed by HUVECs in response to fibrin. Briefly, total RNA was isolated from HUMVEC plated on fibrin in the presence of crude FGF-1 at 0, 2, 5 and 24 hours and subjected to the modified differential mRNA display. One of the clones (D9) isolated from HUMVEC populations exposed to fibrin, which was found to have increased at the 2 hour time-point, was cloned and sequenced. A search of the GenBank database in 1994 demonstrated that the D9 sequence was novel.

The D9 clone (SEQ ID NQ:2) was used as a probe to screen a lambda cDNA library prepared from mRNA obtained from HUVECs exposed to fibrin gels for 1, 3 and 5 hours. Ten isolates were recovered that contained the D9 sequence, two of which appeared, by restriction enzyme analysis, to be spliced variants of the remaining eight. Sequence analysis of the clones revealed that they overlapped to form a contiguous sequence of 5454 base pairs (bp) in length, set forth as SEQ ID NO:2.

Example 2

Figure 2:
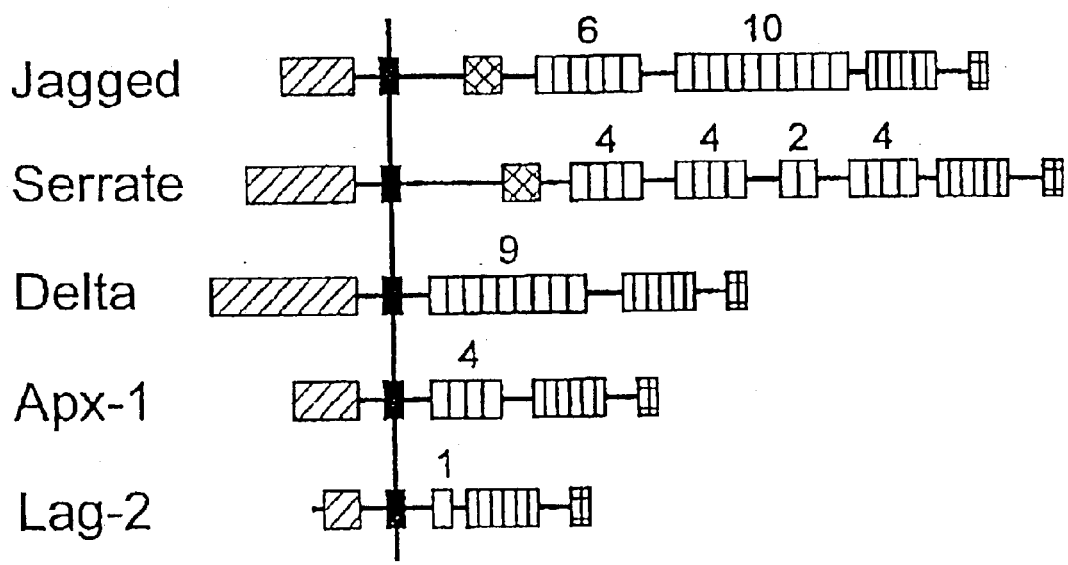
FIG. 2. Illustration of the domain structure of the Notch receptor family. (Numbers refer to the number of EGF repeats in the extracellular domain.) As indicated in this chart, in addition to the 36 EGF repeats within the extracellular domain of Notch 1, there is a cys-rich domain composed of three Notch-Lin-Gip (NLG) repeats, followed by a cys-poor region between the transmembrane and NLG domain. The intracellular domain of Notch 1 contains six ankyrin/Cdc10 repeats positioned between two nuclear localization sequences (NLS). In the carboxy-terminal direction from this region is a polyglutamine-rich domain (OPA) and a pro-glu-ser-thr (PEST) domain. Comparable structures are shown for Lin-12 and Glp-1.
Figure 3:
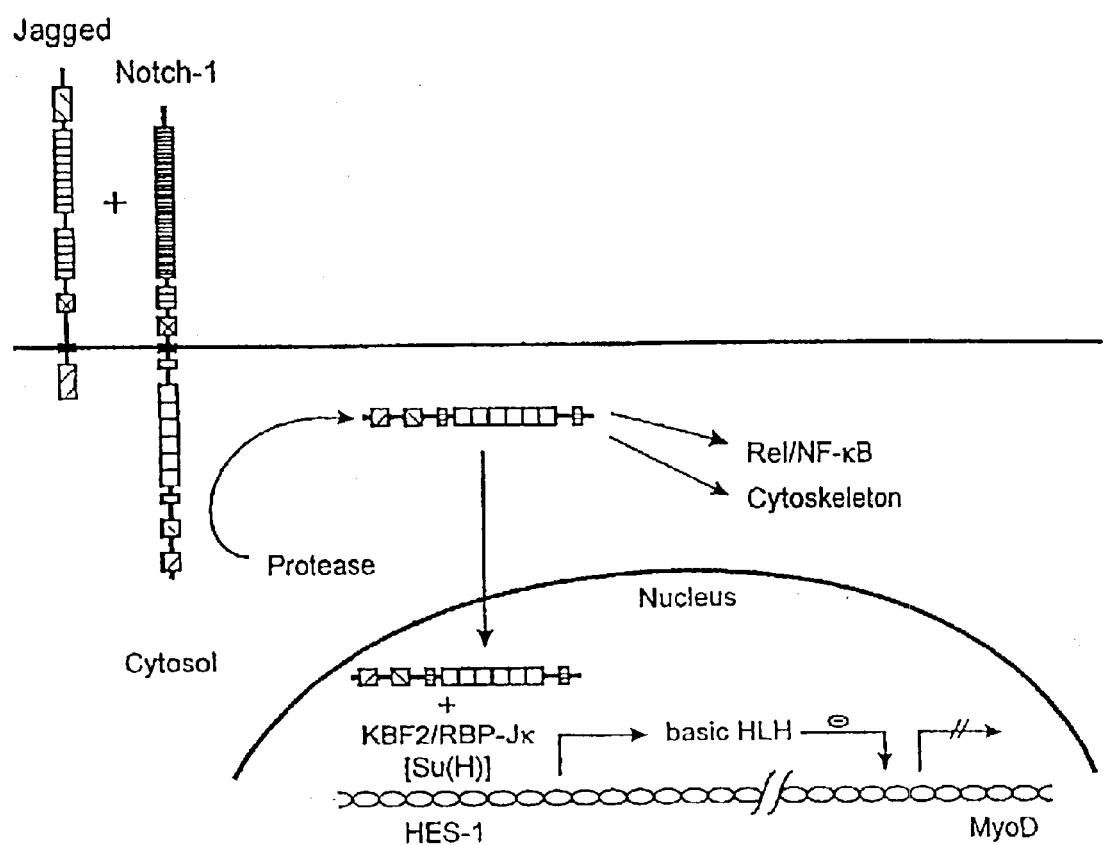
FIG. 3. The Notch signaling pathway. The components of the Notch signaling pathway are illustrated, using the myoblast as an example. The Notch signaling pathway, when activated by Jagged in the endothelial cell, involves cleavage of the intracellular domain by a protease, nuclear trafficking of the Notch fragment and the interaction of this fragment with the $KBF_2$/RBP-Jk transcription factor, a homolog of the *Drosophila* Suppressor of Hairless (Su(H)) gene, which is a basic helix-loop-helix transcription factor involved in Notch signaling.
Figure 4:
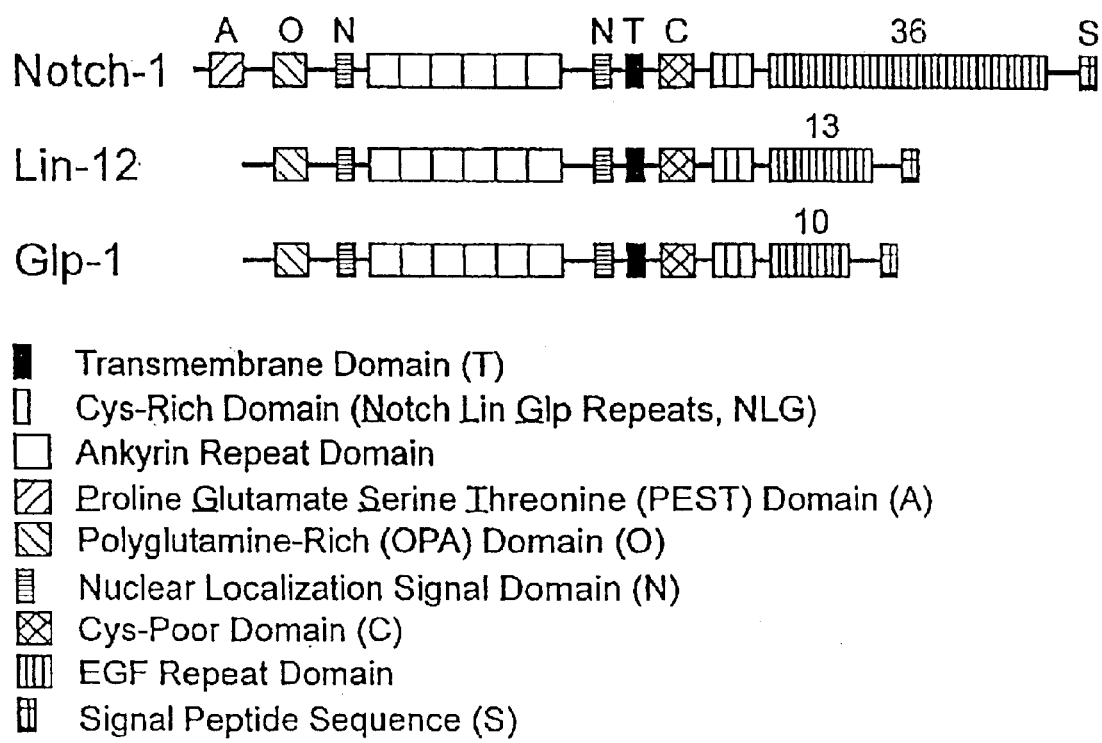
FIG. 4. Illustration of the domain structure of the Notch ligand family. (Numbers refer to the number of EGF repeats in the extracellular domain.) As indicated in this chart, although the intracellular domain of the Jagged gene contains a sequence with no known homology to intracellular regions of other transmembrane structures, the extracellular region of the gene contains a cys-rich region, 16 epidermal growth factor (EGF) repeats, and a Delta-Serrate-Lag (DSL) domain, typical of comparable regions found in other genes including the *Drosophila* ligands, Serrate and Delta, and the *C. elegans* genes, Apx-1 and Lag-2.

Analysis of the Sequence of HUVEC Clone D9 Demonstrates Homology with the Rat Jagged Gene A second search of the Genebank database in 1995 revealed that the D9 clone was very homologous to the cDNA sequence coding for the rat Jagged gene (Lindsell et al., 1995), a ligand for the Notch receptor. Computer analysis revealed an 87% identity at the nucleotide level and a 95% identity at the amino acid level. The Jagged protein contains a putative signal sequence, a DSL domain which describes a consensus region present in other Notch ligands (Delta, Serrate, Lag-2 and Apx-1), an EGF-like repeat domain containing 16 EGF repeats, a cys-rich domain, a transmembrane domain, and a 125 residue cytosol domain. This structure is represented in FIG. 2. Thus, it was determined that clone D9 represents the human homolog of the rat Jagged cDNA.

Two additional Jagged clones were also obtained each containing identical deletions. The first was 89 bp in length, and was located in the middle of the cys-rich region. The second occurred 366 bp downstream from the first region, and was 1307 bp in length. The first deletion predicts a frame-shift in the translation product, resulting in a unique 15 amino acid sequence followed by a premature termination of the protein, effectively deleting the transmembrane and cytosol domain from the Jagged structure.

Example 3
Human Endothelial Cell Populations Express Both Jagged and Notch Transcripts To ascertain that both the human Jagged gene and its putative receptor, Notch, were expressed in the HUVEC population, oligonucleotide primers were designed based upon the published sequence for the human Tan-1 transcript (Notch-1) and the human Notch group protein transcript (Notch-2), as well as for the human Jagged transcript.

Total RNA was obtained using standard protocols. The differential display was performed as previously described by Folkman and Haudenschild, *Nature* 288:551–556 (1980). Briefly, 1 µg of total RNA was reverse transcribed with 200U M-MLV reverse transcriptase (BRL) in the presence of 2 µM of the 3' primer (5'-GCGCAAGCT$_{12}$CG-3') and 100 µM dNTP for 70 minutes at 37° C. The cDNA was amplified in the presence of ($^{32}$P) dATP (Amersham) using the same 3' primer and a 5' primer with the sequence 5'-GAGACCGTGAAGATACTT-3' and the following parameters: 94° C. 45 seconds, 41° C. 1 minute, 72° C. 1 minute for 4 cycles, followed by 94° C. 45 seconds, 60° C. 1 minute, 72° C. 1 minute for 18 cycles. The resulting cDNA species were separated using polyacrylamide gel electrophoresis, the gel was dried and exposed to radiographic film, and the band of interest was cut out of the gel and eluted.

The cDNA was amplified using the same primers and cloned into a TA vector (Invitrogen). The clone was used to screen a cDNA library made in the ZAP Express vector (Stratagene) using RNA isolated from HUVEC plated on fibrin in the presence of crude FGF-1 for 1, 3, 5, 8 and 24 hours to analyze the steady-state levels of the transcripts for Jagged, Notch 1, Notch 2, and GAPDH. See, Garfinkel et al., submitted *J. Cell Biol.* 1996. The overlapping cDNA clones obtained were sequenced using an ABI DNA synthesizer and assembled with the DNASTAR program. RT-PCR analysis was performed as described using the following primers:

Example 4
The Role of Jagged as a Mediator of Microvascular Sprout Formation In Vitro Because (i) Delta/Serrate signaling through Notch is involved in the determination of cell fate in invertebrates (Fortini and Artavanis-Tsakonas, 1993), (ii) Jagged signaling through Notch attenuates the terminal differentiation of myoblasts to myotubes in vitro (Lindsell et al., 1995), (iii) the endothelial cell presents a non-terminal differentiated phenotype in vitro (FIG. 1), and (iv) the Jagged transcript was identified as an endothelial cell differentiation-induced gene, it was important to determine whether Jagged-Notch signaling in the endothelial cell was involved in the early phase of the differentiation pathway. It is well known that endothelial cell sprout formation is an early event in the microvasculature during angiogenesis (Montesano et al., 1985); and endothelial cell sprout formation assays are described in the art (Montesano et al., *Proc. Natl. Acad Sci. USA* 83:7297–7301 (1986)). However, to assess the role of Jagged-Notch signaling in this system, an antisense (γ) oligonucleotide was needed, based on the Jagged sequence to repress the translation of the Jagged transcript.

The γ-Jagged oligomer contained the Kozak sequence, the ATG translation start site and extended three codons into the open-reading frame. Similar γ-oligomers have proven useful in a wide variety of cellular systems to repress the translation of specific transcripts, including the human endothelial cell (Maier et al., 1990b; Garfinkel et al., *J. Biol. Chem.* 267:24375–24378 (1992)). The controls for the γ-Jagged oligomer included the sense counterpart, a 3'-antisense oligomer and a mutated 5' antisense oligomer.

Although the complete DNA sequence of the bovine Jagged transcript had not yet been fully defined, a high degree of homology at the 5' end was predicted between the bovine and the human Jagged nucleotide sequence, in view of the fact that the human and rat Jagged polypeptides are 95% identical.

Bovine microvascular endothelial cells (BMEC) were plated onto a collagen gel, grown to confluence in the presence or absence of varied concentrations of the γ-Jagged oligomer. FGF-2 (10 ng/ml) was added at confluence (Montesano et al., 1986), and the length of microvessels (sprouts formed as a result of cellular invasion into the collagen gel) was measured (Pepper et al., *Biochem. Biophys. Res. Comm.* 189:824–831 (1992)). As shown in FIG. 6, exposure to the γ-Jagged oligomer resulted in an increase

```
jagged sense        5'-CCGACTGCAGAATAAACATC-3  (SEQ ID NO:5);

jagged antisense    5'-TTGGATCTGGTTCAGCTGCT-3' (SEQ ID NO:6);

notch 1 sense       5'-TTCAGTGACGGCCACTGTGA-3' (SEQ ID NO:7);

notch 1 antisense   5'-CACGTACATGAAGTGCAGCT-3' (SEQ ID NO:8);

notch 2 sense       5'-TGAGTAGGCTCCATCCAGTC-3' (SEQ ID NO:9);

notch 2 antisense   5'-TGGTGTCAGGTAGGGATGCT-3' (SEQ ID NO:10);

GAPDH sense         5'-CCACCCATGGCAAATTC-CATGGCA-3' (SEQ ID NO:11);

GAPDH antisense     5'-TCTAGACGGCAGGTCAGGTCCACC-3' (SEQ ID NO:12).
```

As shown in FIG. 5, the steady state levels of the Notch-1 and Notch-2 transcripts were not altered in HUVEC populations exposed to fibrin. In contrast, however, the HUVEC Jagged transcript was induced after three hours exposure to fibrin after which time the steady state levels of the Jagged transcript decreased (FIG. 5).

BMEC sprout length in a concentration dependent manner above the level achieved by FGF-2. In contrast, the three control oligomers, a Jagged sense oligonucleotide, a 3' antisense Jagged oligomer, and a mutated 5' antisense Jagged oligomer did not affect the ability of FGF-2 to induce sprout formation in this assay (FIG. 6).

Prior to this experiment, with the possible exception of vascular endothelial cell growth factor (VEGF), no other growth factor/cytokine signal has been disclosed as able to potentiate the ability of FGF to modify BMEC sprout length. This result would not have been previously anticipated since the Jagged gene had been previously identified as a HUVEC-derived differentiation-induced transcript.

Example 5

The Disparate Effect of the Antisense (γ)-Jagged Oligomer on Small and Large Vessel Endothelial Cell Migration Based upon the surprising effect of the γ-Jagged oligomers on the potentiation of FGF-2-induced BMBC sprout formation (Example 4), a simple assay was designed to assess the influence of the γ-Jagged oligomer on BMEC migration, specifically to confirm that interrupting the Jagged-Notch signaling pathway would attenuate the ability of FGF to increase sprout length. Utilizing essentially the system of Sato and Rifin (1988, supra), bovine microvascular endothelial cells (BMEC) were plated on a fibronectin matrix, and grown to confluence in the absence and presence of varied amounts of the γ-Jagged oligomer.

Briefly, $4 \times 10^5$ BMEC and BAEC were grown to confluence in serum-containing media containing 0, 1.25, 2.5, 5 and 6.25 uM jagged antisense oligonucleotide. The monolayers were wounded by scraping them with a razor blade and cellular debris was removed by washing the plates twice with phosphate buffered saline. The cells were incubated for a further 22 hours at 37° C. to confluence, then fixed in 25% acetic acid, 75% methanol and stained with hematoxylin (Sigma). The number of cells migrating from the wound origin were counted to determine the ability of the BMEC population to migrate into the denuded area. The count was made using a light microscope with a grid at 100× magnification. The data represent a mean of multiple experiments done in duplicate, with five microscopic fields counted for each point.

Figure 7A:
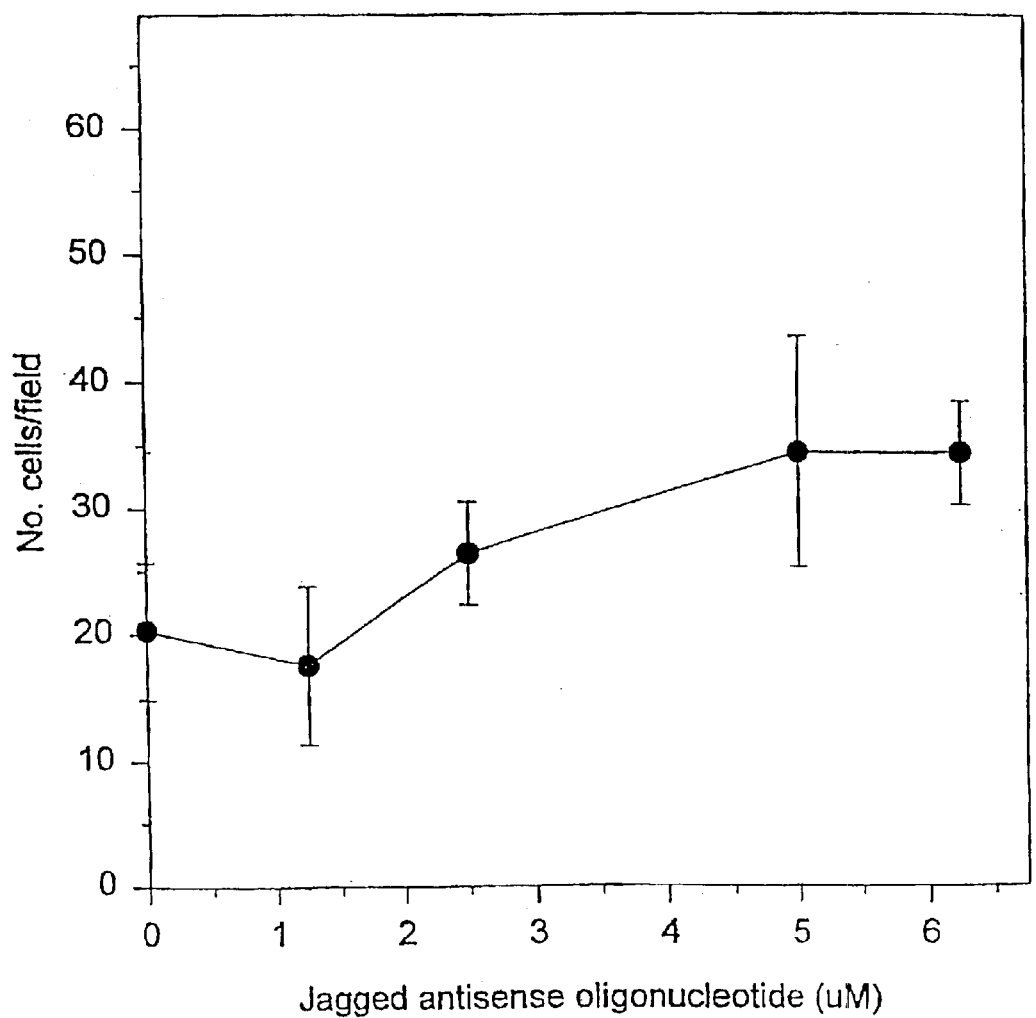
FIGS. 7A and 7B. Line graphs showing the effect of the antisense Jagged oligonucleotide on bovine endothelial cell migration. The effect on bovine microvascular endothelial cells (BMEC) is shown on FIG. 7A; the effect on bovine aorta endothelial cells (BAEC) is shown on FIG. 7B.
Figure 7B:
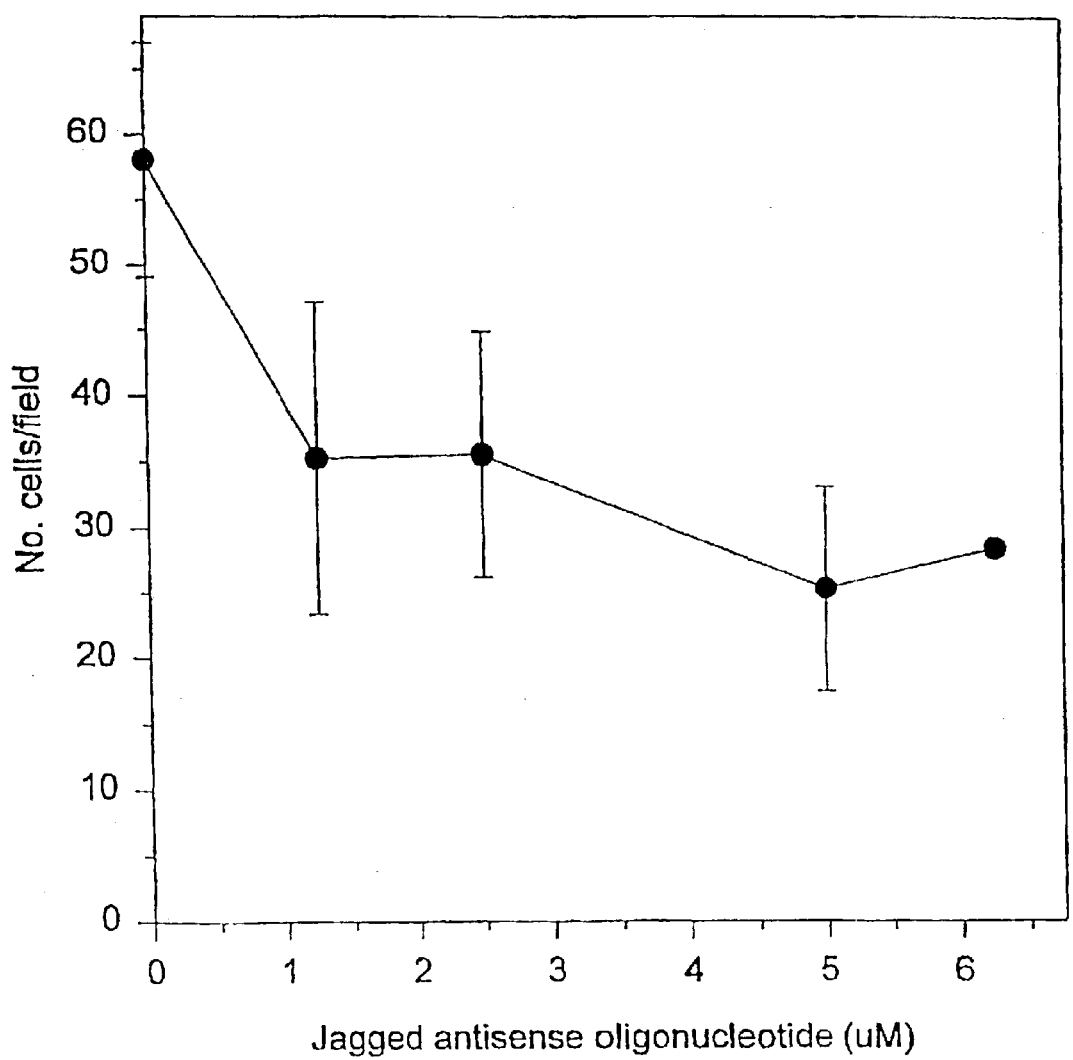

As shown in FIG. 7A, the presence of the γ-Jagged oligomer resulted in an increase in the number of cells migrating into the denuded area with an approximate 80% increase mediated by 5 μM γ-Jagged oligomer. These data (FIG. 7A) agree with the BMEC data obtained from the sprout assay in which 2 μM γ-Jagged oligomer yielded an approximate 100% increase in BMEC sprout length (FIG. 6). Thus, it was shown that an interruption in the Jagged-Notch signaling pathway resulted in an increase in BMEC migration, a major immediate-early component of sprout formation in vitro.

Consequently, an apparent discrepancy was noted between the results of the experiments showing (i) the isolation of the Jagged transcript from a HUVEC population preparing to migrate into a fibrin gel, and (ii) the enhancement of the BMEC by the presumed interruption of the Jagged signal. Noting that the HUVEC are obtained from a macro-vessel, and BMEC are from micro-vessels, the distinction was apparently directly related to the nature of the source of the endothelial cells.

To ascertain that the difference was based upon the type of the endothelial cell (macro-versus micro-vasculature), and not due to variations in the extracellular matrix or the function of growth factors/cytokines in the particular system, an experiment was designed in which the endothelial cells were obtained from the same species, but exclusively from a macrovascular source—bovine aorta endothelial cells (BAEC). BAEC were introduced onto a fibronectin matrix, grown to confluence in the absence and presence of various amounts of the γ-Jagged oligomer, and their migration assessed in a manner identical to that used to assess BMEC migration. As shown in FIG. 7B, there was a concentration-dependent decrease in the migration of the BAEC population in response to the γ-Jagged oligomer with an approximate 50% reduction in BAEC migration at 5 μM γ-Jagged oligomer.

When viewed together, these results indicated Jagged-Notch signaling as an anti-migratory event in the endothelium comprising the microvasculature, but as a pro-migratory event in the endothelium of large vessels. These experiments demonstrated for the first time that there apparently exists a major phenotype difference between small and large vessel endothelial cells in response to a ligand-receptor signaling pathway in the endothelial cell which is modulated during the migratory phase of angiogenesis.

Example 6

Further Characterization of the Disparate Effects Mediated by Jagged-Induced Signaling In Vitro Using Human Endothelial Cells To better understand the mechanism utilized by human endothelial cells to regulate angiogenesis in man, it is important to study the effect of the γ-Jagged oligomer on cell migration using human microvascular endothelial cells and human endothelial cells from large vessels. Although it would be preferable to obtain stable human endothelial cell γ-Jagged transfectants/transductants using conventional gene transfer methods, none have proven useful with regard to human diploid endothelial cells. in vitro. Therefore, the γ-Jagged oligomer strategy is employed as a means to modify the translational efficiency of the human Jagged transcript.

Initially, however, two methods are used to confirm that the γ-Jagged oligomer is able to reduce the efficiency of Jagged translation. Each utilizes rabbit anti-Jagged antibodies being prepared against individual synthetic peptides derived from the extracellular DSL domain, the extracellular cys-poor domain ($NH_2$-terminal to the transmembrane domain) and the intracellular domain of the predicted Jagged protein sequence. Immunologic methods parallel those previously used for the production and purification of antibodies against synthetic peptides derived from sequence analysis of the FGF-1 receptor (Prudovsky et al., J. Biol. Chem. 269:31720–31724 (1994)), cortactin (Zhan et al., 1994) and FGF-1 (Imamura et al., Science 249:1567–1570 (1990)) translation products. Synthetic peptides are prepared as multiple antigen peptides (MAP) using fmoc MAP resins from Applied Biosystems. Likewise, Notch-1 antibodies are also prepared using sequence from the extracellular LNG domain and intracellular ankyrin repeat domain for MAP synthesis.

The first method utilizes hybrid selection, using an immobilized Jagged oligomer to capture the Jagged transcript from HUVEC populations, followed by ($^{35}$S)-met/cys translation of the Jagged transcript in the rabbit reticulocyte system in the absence and presence of varied amounts of the γ-Jagged oligomer. Immunoprecipitation of the Jagged protein followed by SDS-PAGE autoradiography establishes the ability of the γ-Jagged oligomer to repress Jagged translation in vitro.

The second method utilizes HUVEC populations metabolically labeled with ($^{35}$S)-met/cys for Jagged immunoprecipitation from cells exposed to fibrin for 0, 1, 2 and 3 hours. Immunoprecipitation of the Jagged protein from the fibrin-induced HUVEC population followed by SDS-PAGE autoradiography permits a comparative assessment of whether pretreatment of the cells with the γ-Jagged oligomer represses the level of the Jagged protein as a cell-associated polypeptide. The success of these strategies is based upon the fact that the Jagged protein sequence is rich in cys residues, and as a result is metabolically labeled to a high specific activity. Likewise, an accurate molecular weight is assigned to the Jagged protein since competition with synthetic peptide, pre-immune serum, as well as denatured γ-Jagged antiserum, are used as controls to define the specificity of band assignment. Since the predicted Jagged translation product contains 1197 amino acids, the molecular weight is in the 135 to 145 kDa range.

The disparate migratory behavior of the BMEC and BAEC populations is confirmed using stable γ-Jagged transfectants. Since bovine cells are more amenable than HUVEC populations to gene transfer methods, the pMEXneo vector (Martin-Zanca et al., *Mol. Cell. Biol.* 9:24–33 (1989)) is used to select for stable BMEC and BAEC γ-Jagged transfectants as previously described (Zhan et al., 1992). Stable clones are obtained using G418 resistance to quantify the migratory potential of these cells relative to insert-less vector control transfectants. The wound-induced migration assay (Example 6; FIG. 7) is useful to demonstrate that the serum-induced migration potential of the BMEC γ-Jagged transfectants is increased, and the serum-induced migration potential of the BAEC γ-Jagged transfectants is decreased.

Use of these transfectants permits a more rigorous quantification of the disparate modulation of migratory potential between small and large vessel endothelial cells using the conventional Boyden chamber assay previously used to establish the chemotactic activity of FGF-1 (Terranova et al., *J. Cell Biol.* 101:2330–2334 (1985)). In addition, this approach also confirms the assessment of the ability of the BAEC γ-Jagged and insert-less vector control transfectants to respond to the FGF prototypes as inducers of sprout formation in vitro (FIG. 6). Lastly, this strategy permits an assessment of the migratory responsiveness of additional bovine endothelial cells obtained from alternative anatomic sites, including the portal vein, saphenous artery and vein, and adipose-derived microvascular endothelial cells. The ability of these cells to induce steady-state levels of Jagged and Notch receptor transcripts in response to fibrin is also evaluated by RT-PCR analysis as in Example 3 (FIG. 5).

A nuclear run-on analysis of BMEC and BAEC populations, as well as a kinetic analysis of the presence of the Jagged transcript in actinomycin D- and cycloheximide-treated cells in response to fibrin, is employed to determine whether the induction of the Jagged transcript is due to a transcriptional regulatory event and whether Jagged transcript stability is involved in the fibrin response. This analysis is analogous to a previous study on the post-transcriptional regulation of IL-1α in HUVEC populations by Garfinkel et al., *Proc. Natl. Acad. Sci. USA* 91:1559–1563 (1994). Nuclear run-on analysis is performed by incubating nuclei obtained from either BMEC or BAEC populations exposed to fibrin for 0, 1, 3 and 6 hours with 100 μCi of ($^{32}$P)-UTP for 30 minutes. This is followed by the isolation of nascent RNA transcripts, and slot blot analysis using 5 μg of the linearized, denatured and immobilized Jagged cDNA and hybridization at high stringency with the labeled RNA. Glyceraldehyde-3-phosphate dehydrogenase (GAPDH) is used as a positive control, and densitometric values are normalized to the GAPDH signal. Although the level of the Jagged transcript may be difficult to predict, a Jagged signal should be visible. Testing the γ-Jagged oligomer at varied levels permits a determination of the ability, if any, of the γ-Jagged oligomer to access the transcriptional machinery in this system.

The analysis of the affect of the novel protein on human endothelial cells effectively employs the HUVEC population as a model, in comparison with HU artery (A) EC and human cells obtained from other anatomic sites, including, e.g., human adipose-derived microvascular endothelial cells (HMEC), human dermis-derived capillary endothelial cells (HCEC) and human saphenous vein (HSVEC) and artery (HSAEC), available from commercial and academic sources. The addition of the γ-Jagged oligomer to these populations of human endothelial cells will be similar to that described in the protocols involving bovine endothelial cell populations. Thus, the ability of the γ-Jagged oligomer to modulate sprout formation of human capillary, artery and vein endothelial cells is assessed using the collagen invasion assay described in FIG. 6, and the migration wound assay described in FIG. 7 supplemented with a Boyden chamber chemotaxis assay as previously described (Terranova et al., 1985). The resulting data, similar to those obtained with the bovine endothelial cell populations, confirms the above-described conclusion (Examples 4 and 5) that reduction in the translational efficiency of the Jagged transcript (i) increases human microvascular endothelial cell sprout formation and migratory/chemotactic potential and (ii) reduces these activities in the human endothelial cell populations derived from arteries and veins.

To determine in those endothelial cell populations that are induced by the γ-Jagged oligomer to decrease tube formation, it is useful to evaluate whether there is a modification of the steady state transcript levels of the immediate-early endothelial differentiation genes (edg genes). This establishes whether the effect of the γ-Jagged oligomer occurs during immediate-early or mid-to-late phase of the endothelial cell differentiation pathway and supplements the qualitative data with respect to the modification of lumen formation in vitro. While the end point for this assay will be a qualitative assessment of lumen formation as previously described (Jaye et al., 1985), cells will be harvested as described in Example 3 (FIG. 5) for Northern blot analysis of the presence or absence of the edg genes, such as the G-protein-coupled orphan receptor, edg-1 (Hla and Maciag, 1990b), the transcription factor, edg-2 (Hla et al., *Biochim. Biophys. Acta* 1260:227–229 (1995)), cyclooxygenase-2 (cox-2) (Hla and Neilson, *Proc. Natl. Acad Sci. USA* 89:7384–7388 (1992)), and tissue collagenase, among others (Hla and Maciag, 1990a).

Because the data indicate that the γ-Jagged oligomer accelerates capillary endothelial cell migration and sprout formation in vitro, the addition of the Jagged protein to these systems will have the opposite effect—inhibiting capillary endothelial cell migration and sprout formation and promoting large vessel-derived endothelial cell migration in vitro. However, two approaches may be used to evaluate this premise. The first involves the expression and purification of the Jagged polypeptide as a recombinant protein, and the second involves the expression of an extracellular and soluble Jagged construct. Although the predicted Jagged sequence does not contain any recognizable post-translational modification motif in the extracellular domain of the protein, such as N-glycosylation, it is possible that a subtle modification of the Jagged protein will affect the activity of Jagged as a Notch ligand.

Using the recombinant Jagged protein, it is possible to assess its ability to signal through the Notch-1 receptor using a rat myoblast system. Since it has been demonstrated that the rat myoblast cell line, C2C12, transfected with the Notch-1 cDNA will not form myotubes when co-cultured with a lethally irradiated population of murine fibroblast transfected with the rat Jagged cDNA (Lindsell et al., 1995), it is assumed that the parental $C_2C12$ is a Notch-1-deficient cell line. Therefore, the C2C12 cell represents a model cell type to assess the biological function of recombinant Jagged.

The C2C12 cell Notch-1 transfectants, but not C2C12 insert-less vector transfectants, presumably are unable to form myotubes if the recombinant Jagged protein is functional as a ligand. Thus, this system also permits an assessment of the value of Notch-2 as a Jagged receptor.

C2C12 cells are transfected with the full length rat Notch-1 and Notch-2 cDNA containing tandem copies of the influenza virus hemagglutinin (HA) epitope and stable transfectants obtained as described (Zhan et al., 1992). The expression of the Notch-1 and Notch-2 receptor transcripts is monitored by RT-PCR and Northern blot analysis and the protein levels assessed by immunoprecipitation/Western blot analysis of the HA epitope. The addition of the recombinant Jagged ligand (1 ng to 10 µg titration) permits the Notch-1 and Notch-2 C2C12 cell transfectants to repress myotube formation, as assessed by morphologic criteria as well as by the repression of the steady-state levels of the myogenin transcript. These data also define the specific activity of the recombinant Jagged protein for stability studies (temperature, pH, ionic strength as a function of time). An appropriate positive control for these experiments is a population of lethally-irradiated NIH 3T3 cells transfected with the full-length Jagged cDNA to the Notch-1 and Notch-2 C2C12 cell transfectants, insuring the attenuation of myotube formation.

After the specific activity of the soluble Jagged protein is established, it will be possible to assess the ability of the Jagged ligand in a concentration dependent matter to inhibit microvessel endothelial cell migration, chemotaxis and sprout formation in vitro, as in FIGS. 5 and 6. Effective levels of Jagged protein, similar to those previously functional in the C2C12 cell Notch-1 transfectants, are expected to also be functional in the human and bovine microvascular endothelial cell systems. A comparable evaluation involves a determination of the function of the Jagged protein as an inducer of large vessel-derived human and bovine endothelial cell migration, chemotaxis, and sprout formation. A concentration-dependent response is indicated. As described above, the co-culture of the large and small vessel-derived endothelial cells with lethally irradiated NIH 3T3 cell Jagged transfectants and insert-less vector transfectants provides a suitable control to demonstrate the disparate role of Jagged-Notch signaling in the regulation of endothelial cell migration.

Example 7
The Relevance of Jagged-Induced Signaling In Vitro to Angiogenesis In Vivo Because Jagged was cloned as a fibrin-responsive gene in vitro, an in vivo angiogenic system is needed which closely mimics the in vitro system. Traditional angiogenesis assays, such as the chicken chonoallantoic membrane (CAM) (Scher et al., Cell 8:373–382 (1976)) assay or the rabbit cornea assay (Folkman et al., Science 221:719–725 (1983)), are useful for an end-point analysis, and are readily available in the art. However, the complexity of the many individual steps in the angiogenic cascade FIG. 1), and their control by gene regulation, demands a novel in vivo approach that addresses this complexity more specifically.

Plating HUVEC on fibrin has been selected to meet the need for such an in vivo system. It has proven to mimic in vivo, in a reproducible fashion, the in vitro system we used initially to induce and isolate the human Jagged cDNA. The in vivo system involves the subtotal occlusion of a large vessel, such as a carotid or iliac artery with a thrombus, producing an intimal injury. This is typically followed within two days, by migration of endothelial cells into the three-dimensional platelet/fibrin scaffold tube formation. After approximately 4 weeks the system characteristically displays tube perfusion, recruitment of pericytes, and selection of preferred channels with downsizing of minor vessels. Together with the vessels, stromal cells appear as well, contributing to the unique extracellular matrix of this tissue, and making this natural, in vivo system (involving revascularization of an experimental thrombus) ideal for demonstrating the role of Jagged and its receptor(s) in two of the early steps of angiogenesis.

Endothelial migration and tube formation can be separated in time (at 2, 4, 6, 8 days after thrombosis), as well as in space. The migrating cells are primarily located in the central region of the thrombus, whereas the peripheral cells have already formed tubes, as indicated by the appearance of junctions and, almost concomitantly, the arrival of circulating red blood cells.

The antibodies developed for use in this experimental system were designed for use with known immunoperoxidase or immunofluorescence techniques to localize endogenous Jagged and Notch (Nabel et al., 1993). However, an advantage of using this in vivo system is that the experimentally-induced thrombus can be seeded with genetically modified cells, γ-Jagged oligomer, or soluble Jagged protein as described above for the in vitro approach, to influence two distinct phases of the angiogenic cascade in a controlled fashion.

The source of these endothelial cells is from large vessels, but they behave like capillaries when they migrate and form tubes, until some, but not all, will recruit pericytes and smooth muscle cells and assume the appearance and function of large vessels again. Clinically, both in the coronary and in the peripheral circulation, this revascularization process is critical, since successful recanalization of occluding thrombi is highly beneficial to the patient, but its regulation has been poorly understood.

Although an expert qualitative pathologic-anatomical evaluation of the vascular morphology is essential in these in vivo experiments, there are a number of time points that are amenable to quantitative morphometric analysis. This is especially relevant since these time points represent distinct stages in this process. At 4, 6, and 8 days, the number of invading cells are directly counted using a light microscope to evaluate cross-sections. Using immunohistochemical analysis with the CD34 antibody, the relative number of migrating endothelial cells is quantifiable; and using the leukocyte common antigen, the inflammatory cells can be assessed. Unfortunately, smooth muscle cell α-actin cannot be used as a reliable marker for myofibroblasts at this stage, since their phenotype is altered. However, by subtraction, the number of non-endothelial cells can be determined.

Thus, quantification of this early phase indicates whether, and in which direction, the interplay between Jagged and Notch influences the migratory component of the angiogenic process. Using serial sections of the same preparations, the proliferative cell nuclear antigen is usefull to evaluate the relative contribution of proliferation to the total number of cells that populate the thrombus. When the thrombus is seeded with transfected cells expressing soluble Jagged, the myc reporter gene is used to recognize and count these components within the system.

Quantification of the functional vascular lumina in a cross-section after 2 and 4 weeks provides additional insight into the relationship between tube formation and the processes of endothelial migration and proliferation during angiogenesis. This comprises a statistical comparison of the number of individual lumina, grid point counts, and area measurements in perfused vessels. Mechanistically, the Jagged/Notch interaction which initiates tube formation from large vessel endothelial cells in vitro, may prove to be a stop signal for migration and proliferation of the microvasculature.

The endothelial cell site-specific effect of the Jagged-Notch system may also be responsible for the control and coordination of the migration/proliferation/tube formation sequence that ultimately leads to the formation of a new vessel. This can be shown in vivo in a revascularized thrombus murine model system, in which it is possible to deliberately exaggerate or compete with each of the components at the molecular level and at any time point within the process. Indeed, the kinetics of the Jagged/Notch interaction may also be assessable by seeding the thrombus at a later time point with soluble Jagged transfectants.

In the mouse, experimental intervention will involve a surgical exposure of previously treated, occluded carotid artery for an injection of a small volume of either lethally irradiated transfectants, recombinant protein or γ-Jagged oligomer into the site. However, the occluded vessel cannot bleed due to incomplete revascularization. Appropriate controls for the repetitive minor surgical trauma are possible in the same mammal on the contralateral carotid, using cells transfected with an inactive, but minimally altered mutant, inactive recombinant protein, or sense or inactive mutant γ-Jagged oligomers respectively.

While the model is useful to examine the formation of a new three-dimensional network of functioning vascular tubes, an additional model for the reendothelialization of the intima of a large vessel is needed, since Jagged/Notch appears to regulate this process in the opposite direction. Since murine vessels are too small for precise, selective de-endothelialization, the gently ballooned rat thoracic aorta (access from the carotid with a French 2 Edwards balloon) is an appropriate test system since it offers unequivocal starting points, and reasonably accurate quantification (see, Schwartz et al., *Lab. Invest.* 38:568–580 (1978)).

To assess the ability of the Jagged ligand to modify the migration of endothelial cells, thus influencing their ability to form a capillary network and/or to cover a de-endothelialized surface, one of several methods is indicated. In a first method, a therapeutically-effective amount of soluble Jagged ligand is administered intravenously to mice and/or rats prior to and/or following thrombosis or balloon injury. In an alternative method, a thrombotic occlusion in a mouse is seeded with an effective amount of lethally irradiated NIH 3T3 cell soluble Jagged:myc transfectants. While in a third method, in both rats and mice, a distal site is seeded with an effective amount of lethally irradiated NIH 3T3 cell soluble Jagged:myc transfectants onto a subcutaneous fibrin matrix implant, which has been pretreated with lethally irradiated NIH 3T3 cells transfected with a hst-sp-FGF-1 construct using the nude mouse (Forough et al., *J. Biol. Chem.* 268:2960–2968 (1993)).

It is known that the NIH 3T3 cells hst-sp-FGF-1 transfectants ($10^5$ cells) are able to secrete FGF-1 as an extracellular angiogenesis signal, and establish within 5 to 10 days an aggressive capillary network (Forough et al., 1993). This is a result of the ligation of the signal peptide (sp) sequence from the hst/KS5 (FGF4) gene to FGF-1, which directs the traffic of the hst-sp-FGF-1 chimera into the ER-Golgi apparatus for proteolytic processing of the hst/KS5-sp-sequence and release of FGF-1 as a soluble, extracellular protein. The efficacy of this construct has been established in vivo (Nabel et al., 1993; Robinson et al., *Development* 121:505–514 (1995)).

In the third method, following thrombotic occlusion, the NIH 3T3 cell soluble Jagged:myctransfectants ($10^{6-107}$ cells) are injected into the angiogenic site, enabling the cells to express and secrete the soluble Jagged protein into the vasculature. The levels of plasma-derived Jagged (tail vein samples) are monitored by ELISA using the myc-epitope and Jagged antibodies. The rats are then assessed over time (e.g., 1 to 10 days at 2 day intervals) for re-endothelialition of the denuded artery using Evan's blue staining. The degree of angiogenesis in the occlusion zone in the murine vessels is assessed using morphometric analysis of individual endothelial cells and of the fully developed capillary vessels in histological sections. Indeed, analysis by transmission electron microscopy will clearly demonstrate the involvement of endothelial cell migration and sprout formation in this system.

The assessment of the pharmacologic administration of intravenous soluble Jagged in the first method is based upon a similar end point, but utilizes a sufficient amount of recombinant Jagged to saturate both the Notch-1 and Notch-2 receptor Jagged-binding sites. The number and affinity of Jagged-binding sites on the surface of the murine endothelial cell are quantified in vitro by Scatchard analysis of murine aorta-derived endothelial cells and adipose-derived microvascular endothelial cells using competitive ($^{125}$I)-Jagged binding by the method described for FGF-1 (Schreiber et al., *Proc. Natl. Acad. Sci. USA* 82:6138–6142 (1985)).

The apparent lack of regulation of the Notch-1 and Notch-2 transcripts in the HUVEC population (FIG. 5), predicts a high affinity Kd (pM) with approximately 5–20, 000 Notch-binding sites per cell. The radiolabelling of the Jagged polypeptide utilizes the lactoperoxidase method, followed by removal of free ($^{125}$I) by Sephadex G-50 gel exclusion chromatography, This provides a pharmacologic range for the administration of the ligand. In addition, the availability of ($^{125}$I)-Jagged will demonstrate the expected pharmacokinetic of intravenous Jagged using methods previously successful for FGF-1 (Rosengart et al., *Circ. Res.* 64:227–234 (1989).

In sum, these models should provide an in vivo correlate and in vivo models for Jagged function, demonstrating a predicted increase (25%-35%) in lumen re-endothelialization, and a similar decrease in the formation of capillary structures. In comparisons between the in vivo revascularization and reendothelialization experiments in normotensive animals, and in their spontaneously hypertensive rat counterparts (SHR, commercially available from Charles River with guaranteed hypertension), it has been shown that hypertension has a direct, albeit subtle, effect on the aortic endothelium of these model animals (Haudenschild et al., *Hypertension* 3:148–153 (1981)). The aortic re-endothelialization experiments can be repeated in these rats without modification and with hypertension as the only added variable, however, the thrombus revascularization experiments must also be performed in these rats, since there is no comparable murine hypertension model available. The thrombi have been shown to be readily reproducible in mice, rats and rabbits. Thus, species differences do not pose a technical problem in the in vivo model systems.

Example 8

Expression of Soluble Jagged in the NIH 3T3 Cell Line

To determine the effects of a secreted, extracellular form of Jagged, a modified form of the Jagged gene was synthesized, transfected into the NIH 3T3 cell line, and then to select for those cells producing the protein. To track and monitor the fate of this Jagged molecule, a myc tag (reviewed by Kolodziej and Young, *Methods in Enzymology* 194:508–519 (1991)) was also introduced at the 3' end of the gene. In order to do this, several modifications of the jagged gene were necessary, these are; (1) a Kozak sequence (Kozak, *J. Cell Biol.* 108:229–241 (1989)) was engineered onto the 5' end of the gene to ensure efficient transcription (2) a myc epitope tag placed at the 3' end (3) cloning sites engineered on both the 5' end (EcoRl, BamH1, Sal1 sites) and the 3' end (Xhol site).

The primer pair used for this construction were:

```
5' end: Sense
GACTATGCGAATTCGGATCCGTCGACGCCACCATGG

Anti-sense 5' end:
CAAGTTCCCCCGTTGAGACA
```

```
3' end myc tag construction
3' end/antisense primer
GCATAGTCCTCGAGTTACAAGTCTTCTTCAGAAATAAGCTTTTGTTCTAC
GATGTACTCCATTCG
```

3' end/sense primer
ATGGACAAACACCAGCAGAA

Cycling reactions were as previously described in this application.

The 5' reaction was digested with EcoRl and BglII, the 3' reaction was digested with Xho1 and Acc 1 site. These were ligated via standard protocol into a similarly digested Jagged template. The final gene product was then digested with EcoR1 and Xho1 and ligated into the eukaryotic expression vector pMexNeo2. This was then transfected into the NIH 3T3 cell line and cells grown in selection media containing G418 (as previously described).

Calcium mediated DNA was transferred into NIH 3T3 cells followed by growth in selective media results in clone: Mw38–1.1 which synthesized the anticipated protein and also released it into the surrounding medium (conditioned media).

These 38–1.1 cells showed a unique phenotype. They grossly formed cord-like structures in vitro correlating with the presence of pseudo-lumens by ultrastructure analysis. In addition, they were able to induce wild type NIH to partially assume this phenotype. As such, 38–1.1 would be an outstanding resource both for the production and isolation of the soluble Jagged (sol-jag) protein, and also for its ability to modulate the differentiation pattern of adjacent cells.

Although the present invention has been described with reference to the presently preferred embodiments, the skilled artisan will appreciate that various modifications, substitutions, omissions and changes may be made without departing from the spirit of the invention. Accordingly it is intended that the scope of the present invention be limited only by the scope of the following claims, including equivalents thereof.

---

What is claimed is:

1. A substantially purified nucleic acid encoding a Jagged protein, wherein the nucleotide sequence of said nucleic acid consists of the nucleic acid sequence of SEQ ID NO:2.

2. A composition comprising the nucleic acid of claim 1 and a pharmaceutically acceptable carrier.

3. Vector comprising the nucleic acid of claim 1.

4. A recombinant cell comprising the nucleic acid of claim 1.

5. A substantially purified, single-stranded, complementary nucleic acid molecule complementary to said nucleic acid encoding Jagged of claim 1.

6. A substantially purified nucleic acid molecule encoding a Jagged protein, wherein the amino acid sequence of said Jagged consists of the sequence of SEQ ID NO:1.

7. A composition comprising the nucleic acid of claim 6 and a pharmaceutically acceptable carrier.

8. A vector comprising the nucleic acid of claim 6.

9. A recombinant cell comprising the nucleic acid of claim 6.

10. A recombinant cell comprising the vector of claim 8.

11. A composition comprising the nucleic acid of claim 5 and a pharmaceutically acceptable carrier.

12. A vector comprising the nucleic acid of claim 5.

13. A recombinant cell comprising the nucleic acid of claim 5.

14. A recombinant cell comprising the vector of claim 12.

* * * * *